US012616540B2

(12) United States Patent     (10) Patent No.:    US 12,616,540 B2

Parastegari et al.           (45) Date of Patent:       May 5, 2026

(54) IMAGING DEVICE CONTROL VIA MULTIPLE INPUT MODALITIES

(71) Applicant: INTUITIVE SURGICAL OPERATIONS, INC., Sunnyvale, CA (US)

(72) Inventors: Mohammad Sina Parastegari, Cupertino, CA (US); Paul G. Griffiths, Santa Clara, CA (US); Brandon D. Itkowitz, San Jose, CA (US); Goran A. Lynch, Oakland, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 415 days.

(21) Appl. No.: 18/256,476

(22) PCT Filed: Dec. 8, 2021

(86) PCT No.: PCT/US2021/062466

§ 371 (c)(1),
(2) Date: Jun. 8, 2023

(87) PCT Pub. No.: WO2022/125699

PCT Pub. Date: Jun. 16, 2022

(65) Prior Publication Data

US 2024/0024049 A1     Jan. 25, 2024

Related U.S. Application Data

(60) Provisional application No. 63/123,939, filed on Dec. 10, 2020.

(51) Int. Cl.
   *A61B 34/37*       (2016.01)
   *A61B 34/00*       (2016.01)
          (Continued)

(52) U.S. Cl.
   CPC .............. *A61B 34/37* (2016.02); *A61B 34/74* (2016.02); *A61B 34/76* (2016.02); *A61B 34/77* (2016.02);
          (Continued)

(58) Field of Classification Search
   CPC .......................... A61B 34/74; A61B 34/30–37
   See application file for complete search history.

(56)          References Cited

U.S. PATENT DOCUMENTS 5,876,325 A    3/1999   Mizuno et al.
6,424,885 B1   7/2002   Niemeyer et al.
         (Continued)

FOREIGN PATENT DOCUMENTS

WO    WO-2020028777 A1    2/2020
WO    WO-2021041248 A1    3/2021
         (Continued)

OTHER PUBLICATIONS

International Search Report and Written Opinion for Application No. PCT/US2021/062466, mailed May 27, 2022, 16 pages.
         (Continued)

*Primary Examiner* — Angela M Hoffa

(74) *Attorney, Agent, or Firm* — Artegis Law Group, LLP

(57)          ABSTRACT

Techniques are disclosed for imaging device control in a computer-assisted device that includes a repositionable structure configured to support an imaging device, and a control system configured to determine a position of a first reference point associated with a first input modality; in a first mode, determine a position of a target reference point for the imaging device based on the first reference point; in a second mode, determine a position of a second reference point associated with a second input modality, and determine the position of the target reference point based on the position of the first reference point and the position of the (Continued)

second reference point; determine a movement of the first repositionable structure that moves the imaging device such that a third reference point associated with the imaging device moves toward the target reference point; and cause actuation of the repositionable structure based on the movement.

21 Claims, 10 Drawing Sheets

(51) Int. Cl.
| | |
|---|---|
| *A61B 34/30* | (2016.01) |
| *A61B 90/00* | (2016.01) |
| *A61B 90/50* | (2016.01) |

(52) U.S. Cl.
CPC .............. *A61B 90/37* (2016.02); *A61B 90/50* (2016.02); *A61B 2034/301* (2016.02)

(56)     References Cited

U.S. PATENT DOCUMENTS

| | | | | |
|---|---|---|---|---|
| 8,335,590 | B2 * | 12/2012 | Costa | A61B 34/37 |
| | | | | 700/250 |
| 8,414,469 | B2 * | 4/2013 | Diolaiti | A61B 34/30 |
| | | | | 700/63 |
| 8,423,186 | B2 | 4/2013 | Itkowitz et al. | |
| 8,657,736 | B2 * | 2/2014 | Diolaiti | A61B 34/37 |
| | | | | 700/62 |
| 8,663,091 | B2 * | 3/2014 | Diolaiti | A61B 34/37 |
| | | | | 700/62 |
| 8,808,164 | B2 | 8/2014 | Hoffman et al. | |
| 8,961,399 | B2 * | 2/2015 | Diolaiti | A61B 90/361 |
| | | | | 700/62 |
| 9,179,832 | B2 | 11/2015 | Diolaiti | |
| 9,586,323 | B2 * | 3/2017 | Diolaiti | A61B 34/35 |
| 9,948,852 | B2 * | 4/2018 | Lilagan | A61B 1/00188 |
| 9,955,859 | B2 * | 5/2018 | Diolaiti | A61B 1/00042 |
| 10,532,467 | B2 * | 1/2020 | Diolaiti | A61B 34/35 |
| 10,582,838 | B2 * | 3/2020 | Diolaiti | A61B 1/3132 |
| 10,715,720 | B2 * | 7/2020 | Lilagan | A61B 1/00193 |
| 10,836,045 | B2 * | 11/2020 | Diolaiti | A61B 34/30 |
| 11,284,782 | B2 * | 3/2022 | Diolaiti | A61B 1/00042 |
| 11,290,637 | B2 * | 3/2022 | Lilagan | H04N 23/61 |
| 11,758,262 | B2 * | 9/2023 | Lilagan | H04N 23/61 |
| | | | | 348/45 |
| 11,969,147 | B2 * | 4/2024 | Diolaiti | A61B 1/313 |
| 2010/0161129 | A1 * | 6/2010 | Costa | B25J 9/1697 |
| | | | | 901/47 |
| 2013/0211590 | A1 * | 8/2013 | Diolaiti | B25J 9/1689 |
| | | | | 700/257 |
| 2013/0218171 | A1 * | 8/2013 | Diolaiti | A61B 34/37 |
| | | | | 606/130 |
| 2013/0218172 | A1 * | 8/2013 | Diolaiti | A61B 90/10 |
| | | | | 606/130 |
| 2014/0249544 | A1 * | 9/2014 | Diolaiti | A61B 34/30 |
| | | | | 606/130 |
| 2014/0267626 | A1 * | 9/2014 | Lilagan | A61B 1/00193 |
| | | | | 348/46 |
| 2016/0037998 | A1 | 2/2016 | Kawashima et al. | |
| 2016/0038011 | A1 * | 2/2016 | Diolaiti | A61B 34/74 |
| | | | | 600/424 |
| 2016/0183930 | A1 | 6/2016 | Herzlinger et al. | |
| 2017/0129108 | A1 * | 5/2017 | Diolaiti | A61B 90/361 |
| 2018/0214014 | A1 * | 8/2018 | Diolaiti | A61B 1/045 |
| 2018/0220064 | A1 * | 8/2018 | Lilagan | A61B 1/00188 |
| 2020/0015917 | A1 * | 1/2020 | Cavalier | B25J 13/02 |
| 2020/0139556 | A1 * | 5/2020 | Diolaiti | B25J 13/06 |
| 2020/0163539 | A1 * | 5/2020 | Diolaiti | A61B 1/313 |
| 2020/0222125 | A1 | 7/2020 | Ishihara et al. | |
| 2020/0261160 | A1 * | 8/2020 | Peine | A61B 34/37 |
| 2020/0322526 | A1 * | 10/2020 | Lilagan | H04N 23/62 |
| 2022/0175230 | A1 * | 6/2022 | Diolaiti | A61B 1/045 |
| 2022/0191388 | A1 * | 6/2022 | Lilagan | H04N 23/62 |

FOREIGN PATENT DOCUMENTS

| | | | |
|---|---|---|---|
| WO | WO-2021041249 | A1 | 3/2021 |
| WO | WO-2021041253 | A1 | 3/2021 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2021/062466 mailed Jun. 22, 2023, 11 pages.

\* cited by examiner

A

B

A

B

A

B

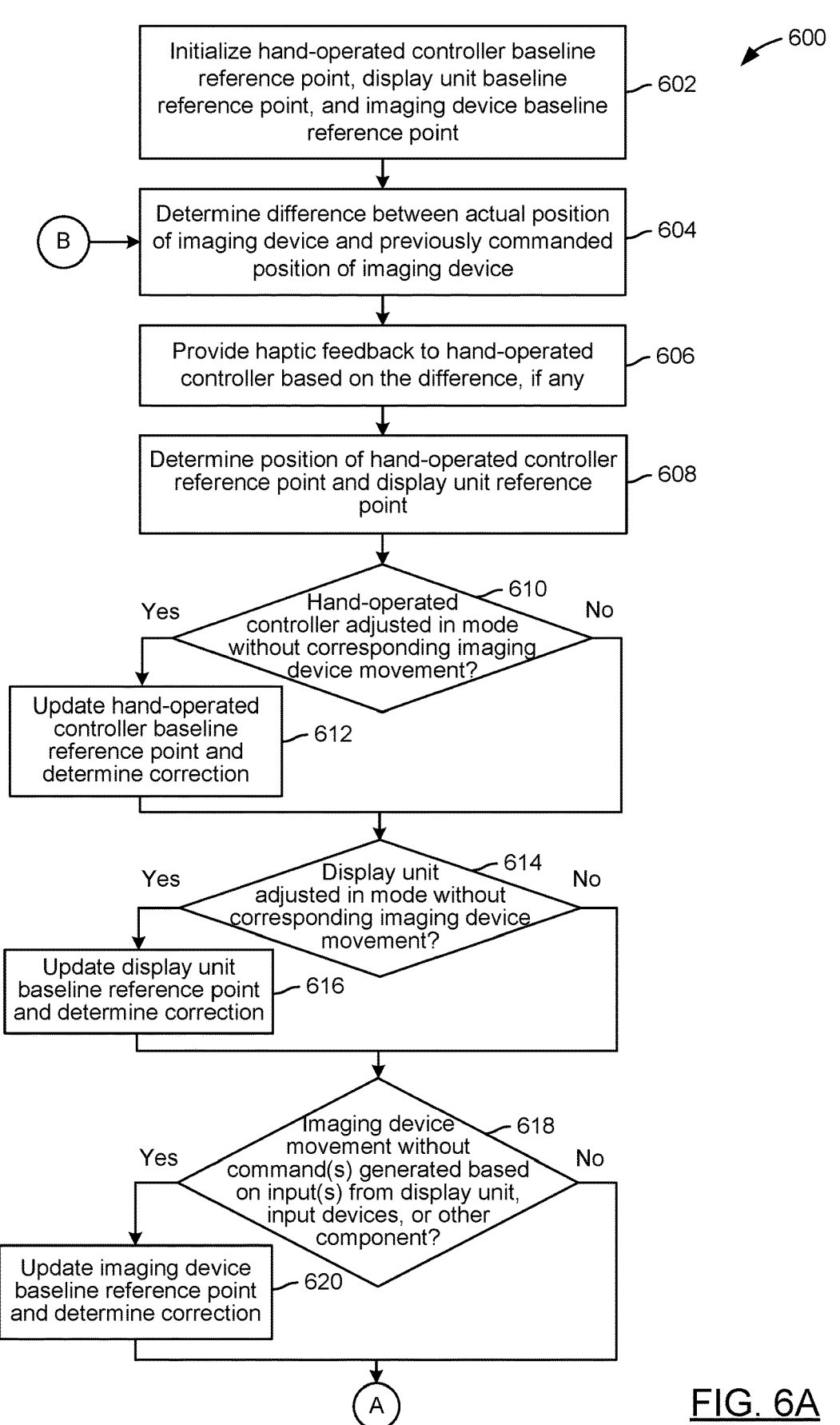

Initialize hand-operated controller baseline reference point, display unit baseline reference point, and imaging device baseline reference point ⟋ 602

Determine difference between actual position of imaging device and previously commanded position of imaging device ⟋ 604

Provide haptic feedback to hand-operated controller based on the difference, if any ⟋ 606

Determine position of hand-operated controller reference point and display unit reference point ⟋ 608

Hand-operated controller adjusted in mode without corresponding imaging device movement? ⟋ 610

Yes / No

Update hand-operated controller baseline reference point and determine correction ⟋ 612

Display unit adjusted in mode without corresponding imaging device movement? ⟋ 614

Yes / No

Update display unit baseline reference point and determine correction ⟋ 616

Imaging device movement without command(s) generated based on input(s) from display unit, input devices, or other component? ⟋ 618

Yes / No

Update imaging device baseline reference point and determine correction ⟋ 620

IMAGING DEVICE CONTROL VIA MULTIPLE INPUT MODALITIES

RELATED APPLICATIONS

This application is a U.S. National Stage patent application of International Patent Application No. PCT/US2021/062466, filed Dec. 8, 2021, and claims the benefit to U.S. Provisional Application No. 63/123,939, filed Dec. 10, 2020, and entitled "Imaging Device Control via Multiple Input Modalities," each of these related applications is incorporated by reference herein.

TECHNICAL FIELD

The present disclosure relates generally to electronic devices, and more particularly to control of devices with repositionable imaging devices.

BACKGROUND

More and more devices are being replaced with computer-assisted electronic devices. This is especially true in industrial, entertainment, educational, and other settings. As a medical example, the hospitals of today have large arrays of electronic devices being found in operating rooms, interventional suites, intensive care wards, emergency rooms, and/or the like. Many of these electronic devices may be capable of autonomous or semi-autonomous motion. It is also common for personnel to control the motion and/or operation of electronic devices using one or more input devices located at a user control system. As a specific example, minimally invasive, robotic telesurgical systems permit surgeons to operate on patients from bedside or remote locations. Telesurgery refers generally to surgery performed using surgical systems where the surgeon uses some form of remote control, such as a servomechanism, to manipulate surgical instrument movements rather than directly holding and moving the instruments by hand.

When an electronic device is used to perform a task at a worksite, one or more imaging devices (e.g., an endoscope, an optical camera, and/or an ultrasound probe) can capture images of the worksite that provide visual feedback to an operator who is monitoring and/or performing the task. The imaging device(s) may also be controllable to update a view of the worksite that is provided, via a display unit, to the operator. For example, the imaging device(s) could be attached to a repositionable structure that includes two or more links coupled together by one or more joints, where the repositionable structure can be moved (including through internal reconfiguration) to update a position and/or orientation of the imaging device at the worksite. In such a case, movement of the imaging device(s) may be controlled by the operator, another person, or automatically, and enable the view of the worksite to be changed.

One approach for controlling an imaging device is to move the imaging device to follow the motion of a display unit. For example, the head motion of an operator can be tracked via a sensor system and used to control the motion of the imaging device. Another approach for controlling an imaging device is to move the imaging device to follow the motion of a hand-operated controller. For example, the operator could control a hand-operated controller with one input device operated by each hand of the operator. These approaches are used separately, and each has its own advantages and disadvantages.

Accordingly, improved methods and systems for controlling repositionable imaging devices are desirable.

SUMMARY

Consistent with some embodiments, a computer-assisted device includes a first repositionable structure configured to support an imaging device; and a control system coupled to the first repositionable structure. The control system is configured to: determine a position of a first reference point associated with a first input modality, in a first mode, determine a position of a target reference point for the imaging device based on at least the first reference point, in a second mode, determine a position of a second reference point associated with a second input modality, and determine the position of the target reference point based on at least the position of the first reference point and the position of the second reference point, determine a movement of the first repositionable structure that moves the imaging device such that a third reference point associated with the imaging device moves toward the target reference point, and cause actuation of the first repositionable structure based on the determined movement.

Consistent with some embodiments, a computer-assisted device includes a first repositionable structure configured to support an imaging device, and a control system coupled to the first repositionable structure. The control system is configured to: determine a position of a first reference point associated with a first input modality, determine a position of a first target reference point based on at least the position of the first reference point, determine whether the first repositionable structure can be actuated to move the imaging device such that a third reference point associated with the imaging device moves to the first target reference point, determine a position of a second reference point associated with a second input modality, determine a position of a second target reference point based on at least the position of the first reference point and the position of the second reference point, determine whether the first repositionable structure can be actuated to move the imaging device such that the third reference point moves to the second target reference point, and in response to a determination that the first repositionable structure can be actuated to move the imaging device such that the third reference point moves to the second target reference point, actuate the first repositionable structure based on the position of the second target reference point.

Consistent with some embodiments, a method of operating a computer-assisted device comprising a first repositionable structure and one or more processors, the one or more processors communicatively coupled to the first repositionable structure, includes determining, by the one or more processors, a position of a first reference point associated with a first input modality; in a first mode, determining, by the one or more processors, a position of a target reference point for an imaging device supported by a first repositionable structure of a computer-assisted device based on at least the first reference point; in a second mode, determining, by the one or more processors, a position of a second reference point associated with a second input modality, and determining the position of the target reference point based on at least the position of the first reference point and the position of the second reference point; determining, by the one or more processors, a movement of the first repositionable structure that moves the imaging device such that a third reference point associated with the imaging device moves toward the target reference point; and causing, by the one or more processors, actuation of the first repositionable structure based on the determined movement.

Consistent with some embodiments, a method of operating a computer-assisted device comprising a first repositionable structure and one or more processors, the one or more processors communicatively coupled to the first repositionable structure, includes determining, by the one or more processors, a position of a first reference point associated with a first input modality; determining, by the one or more processors, a position of a first target reference point based on at least the position of the first reference point; determining, by the one or more processors, whether the first repositionable structure can be actuated to move the imaging device such that a third reference point associated with the imaging device moves to the first target reference point; determining, by the one or more processors, a position of a second reference point associated with a second input modality; determining, by the one or more processors, a position of a second target reference point based on at least the position of the first reference point and the position of the second reference point; determining, by the one or more processors, whether the first repositionable structure can be actuated to move the imaging device such that the third reference point moves to the second target reference point; and in response to a determination that the first repositionable structure can be actuated to move the imaging device such that the third reference point moves to the second target reference point, actuating the first repositionable structure based on the position of the second target reference point.

Other embodiments include, without limitation, one or more non-transitory machine-readable media including a plurality of machine-readable instructions which when executed by one or more processors are adapted to cause the one or more processors to perform any of the methods disclosed herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 6A-6B illustrate a simplified diagram of a method for controlling an imaging device, according to various embodiments.

DETAILED DESCRIPTION

Figure 1:
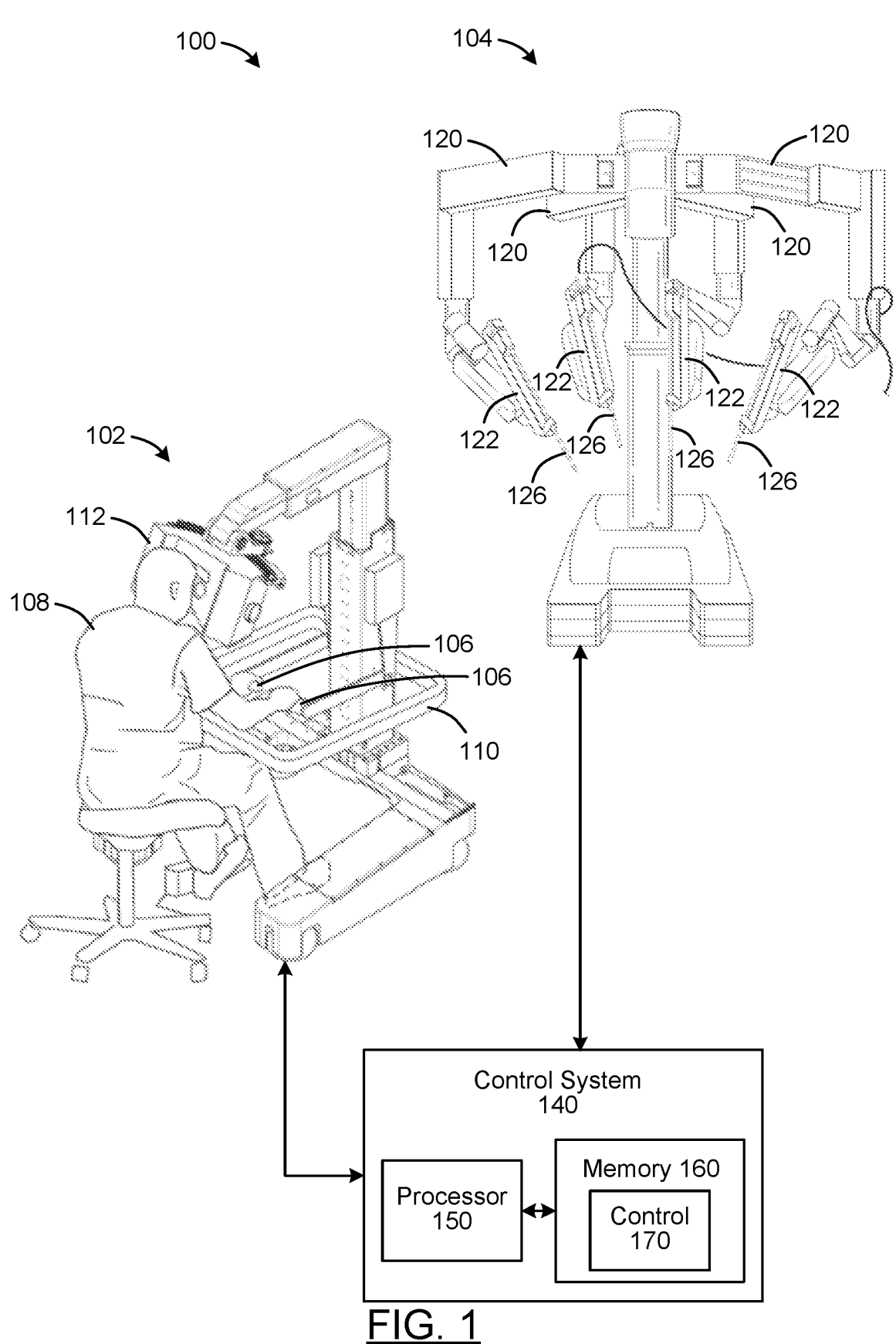
FIG. 1 is a simplified diagram of an example teleoperated system, according to various embodiments.

This description and the accompanying drawings that illustrate inventive aspects, embodiments, embodiments, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, embodiment, or module may, whenever practical, be included in other embodiments, embodiments, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, embodiment, or application may be incorporated into other embodiments, embodiments, or aspects unless specifically described otherwise, unless the one or more elements would make an embodiment or embodiment non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an embodiment using a surgical system, such as the da Vinci® Surgical System commercialized by Intuitive Surgical, Inc. of Sunnyvale, California. Knowledgeable persons will understand, however, that these examples are not limiting and the inventive aspects disclosed herein may be embodied and implemented in various ways, including robotic and, as applicable, non-robotic embodiments. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

System Overview

FIG. 1 is a simplified diagram of an example teleoperated system 100, according to various embodiments. In some examples, the teleoperated system 100 may be a teleoperated medical system such as a surgical system. As shown, the teleoperated system 100 includes a follower device 104 and a leader device in a leader-follower configuration. In the leader-follower configuration, the follower mimics the motion of the leader. The leader device in FIG. 1 is shown as including an input system 102 in the form of a workstation (also called a "console). In various embodiments, the input system 102 may be in any appropriate form and may or may not include a workstation. In the FIG. 1 example, the follower device 104 is controlled by one or more input devices 106 of the input system 102, described in greater detail below. The leader-follower configuration is also sometimes referred to as a master-slave configuration, and systems that include leader and follower devices are also sometimes referred to as master-slave systems, where the leader is the "master," and the follower is the "slave."

In this example, the input system 102 includes one or more input devices which are contacted and manipulated by an operator 108. As shown, the input system 102 includes an input device 106 for use by each hand of the operator. The input devices 106 are supported by the input system 102 and may be mechanically grounded. An ergonomic support 110 (e.g., forearm rest) may be provided in some embodiments, on which the operator 108 may rest his or her forearms. In some examples, the operator 108 may perform tasks at a worksite near the follower device 104 during a procedure by commanding the follower device 104 using the input devices 106.

A display unit 112 is another input device included in the input system 102. The display unit 112 may display images for viewing by the operator 108. The display unit 112 may be moved in various degrees of freedom to accommodate the viewing position of the operator 108 and/or to provide control functions. In the example of the teleoperated system 100, displayed images may depict a worksite at which the operator 108 is performing various tasks by manipulating the input devices 106 and/or the display unit 112. In some examples, the images displayed by the display unit 112 may be received by the input system 102 from one or more imaging devices for capturing images arranged at the worksite. In other examples, the images displayed by the display unit may be generated by the display unit 112 (or by a connected other device or system), such as for virtual representations of tools, the worksite, or for user interface components.

When using the input system 102, the operator 108 may stand, or sit in a chair or other support, position his or her eyes to view the display unit 112, manipulate the input devices 106 and/or the display unit 112, and rest his or her forearms on the ergonomic support 110 as desired. In some embodiments, the operator 108 may stand at the input system 102 or assume other poses, and the display unit 112 and other input devices may be adjusted in position (height, depth, etc.) to accommodate the operator 108.

The teleoperated system 100 may also include the follower device 104, which may be commanded by the leader device, such as by the input system 102. In a medical example, the follower device 104 can be located near an operating table (e.g., a table, bed, or other support) on which a patient may be positioned. In such cases, the worksite may be provided on the operating table, e.g., on or in a patient, simulated patient or model, etc. (not shown). The follower device 104 shown includes a plurality of manipulator arms 120, each configured to couple to an instrument 122. The manipulator arms 120 are examples of repositionable structures on which instruments 122 (such as manipulation instruments or instruments with imaging devices) can be mounted. An instrument 122 may include, for example, an end effector 126 and a housing configured to couple to a manipulator arm 120.

In various embodiments, one or more of the instruments 122 may include an imaging device for capturing images (e.g., optical cameras, hyperspectral cameras, ultrasonic sensors, etc.). For example, one or more of the instruments 122 could be an endoscope that includes an imaging device, which may provide captured images of a portion of the worksite to be displayed via the display unit 112.

In some embodiments, the manipulator arms 120 may be controlled to move, articulate, or actuate the instruments 122 (such as by translating or rotating the entire instrument 122, articulating or actuating the end effector 126, or articulating any instrument joints proximal to the end effector 126) in response to manipulation of input devices by the operator 108, so that the operator 108 may perform tasks at the worksite. For a surgical example, the operator may direct the manipulator arms 120 to move instruments 122 to perform surgical procedures at internal surgical sites through minimally invasive apertures or natural orifices.

As shown, a control system 140 is provided external to the input system 102 and communicates with the input system 102. In other embodiments, the control system 140 may be provided in the input system 102 and/or in the follower device 104. As the operator 108 moves input device(s) 106 and/or the display unit 112, sensed spatial information including sensed position and/or orientation information is provided to the control system 140 based on the movement of the input devices 106 and/or the display unit 112. The control system 140 may determine or provide control signals to the follower device 104 to control the movement of the manipulator arms 120 or instruments 122 based on the received information and user input. In one embodiment, the control system 140 supports one or more wired communication protocols, (e.g., Ethernet, USB, and/or the like) and/or one or more wireless communication protocols (e.g., Bluetooth, IrDA, HomeRF, IEEE 802.11, DECT, Wireless Telemetry, and/or the like).

The control system 140 may be implemented on one or more computing systems. One or more computing systems may be used to control the follower device 104. In addition, one or more computing systems may be used to control components of the input system 102, such as to control movement of a display unit 112 in response to input provided by the head of the operator 108.

As shown, the control system 140 includes a processor 150 and a memory 160 storing a control module 170. In embodiments, the control system 140 may include one or more processors, non-persistent storage (e.g., volatile memory, such as random access memory (RAM), cache memory), persistent storage (e.g., a hard disk, an optical drive such as a compact disk (CD) drive or digital versatile disk (DVD) drive, a flash memory, etc.), a communication interface (e.g., Bluetooth interface, infrared interface, network interface, optical interface, etc.), and numerous other elements and functionalities. In addition, functionality of the control module 170 can be implemented in any technically feasible software and/or hardware.

Each of the one or more processors of the control system 140 may be an integrated circuit for processing instructions. For example, the one or more processors may be one or more cores or micro-cores of a processor, a central processing unit (CPU), a microprocessor, a field-programmable gate array (FPGA), an application-specific integrated circuit (ASIC), a digital signal processor (DSP), a graphics processing unit (GPU), a tensor processing unit (TPU), and/or the like.

A communication interface of the control system 140 may include an integrated circuit for connecting the computing system to a network (not shown) (e.g., a local area network (LAN), a wide area network (WAN) such as the Internet, mobile network, or any other type of network) and/or to another device, such as another computing system.

Further, the control system 140 may include one or more output devices, such as a display device, a printer, a speaker, external storage, or any other output device. Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform some embodiments of the invention.

Continuing with FIG. 1, the control system 140 may be connected to or be a part of a network. The network may include multiple nodes. The control system 140 may be implemented on one node or on a group of nodes. By way of example, the control system 140 may be implemented on a node of a distributed system that is connected to other nodes. By way of another example, the control system 140 may be implemented on a distributed computing system having multiple nodes, where different functions and/or components of the control system 140 may be located on a different node within the distributed computing system. Further, one or more elements of the aforementioned control system 140 may be located at a remote location and connected to the other elements over a network.

In some embodiments, one or more input devices may be ungrounded (ungrounded input devices being not kinematically grounded, and an example ungrounded input device is configured to be held by the hands of the operator 108 without additional physical support provided by hardware). Such ungrounded input devices may be used in conjunction with the display unit 112. In some embodiments, the operator 108 may use a display unit 112 positioned near the worksite, such that the operator 108 may manually operate instruments at the worksite, such as a laparoscopic instrument in a surgical example, while viewing images displayed by the display unit 112.

Some embodiments may include one or more components of a teleoperated medical system such as a da Vinci® Surgical System, commercialized by Intuitive Surgical, Inc. of Sunnyvale, California, U.S.A.

Figure 2:
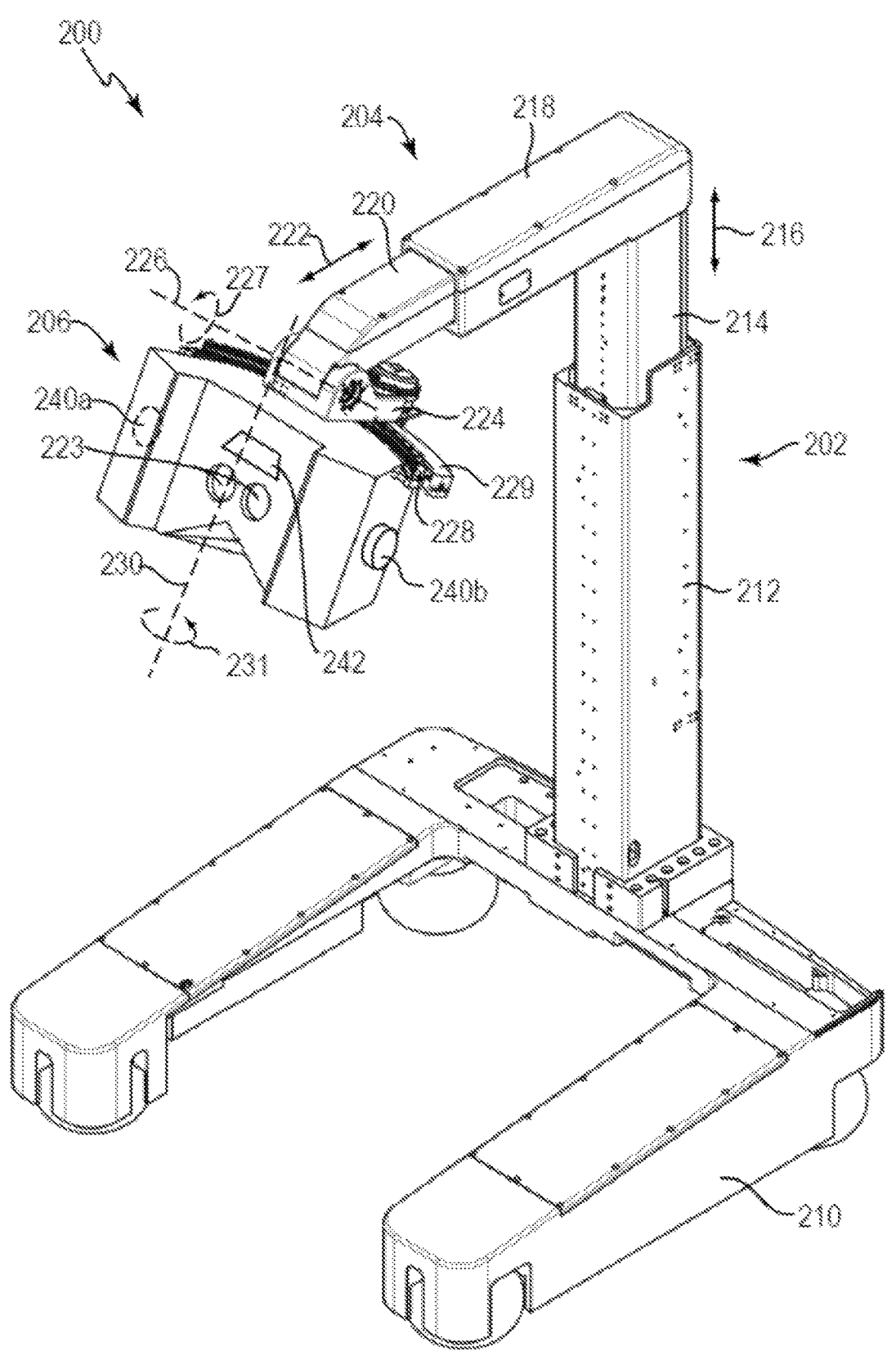
FIG. 2 is a perspective view of an example display system, in accordance with some embodiments.

FIG. 2 is a perspective view of an example display system 200, in accordance with various embodiments. In some embodiments, the display system 200 is used in a workstation of a teleoperated system (e.g., in the workstation shown in FIG. 1), or the display system 200 may be used in other systems or as a standalone system, e.g., to allow an operator to view a worksite or other physical site, a displayed virtual environment, etc. Although FIG. 2 shows a specific configuration, other embodiments may use different configurations.

The display system 200 includes a base support 202, an arm support 204, and a display unit 206. In some embodiments, the display unit 206 is consistent with the display unit 112 in FIG. 1. The display unit 206 is provided with multiple degrees of freedom of movement provided by a support linkage including base support 202, arm support 204 coupled to the base support 202, and a tilt member 224 (described below) coupled to the arm support 204, where the display unit 206 is coupled to the tilt member 224.

The base support 202 may be a vertical member that is mechanically grounded, e.g., directly or indirectly coupled to ground, such as by resting or being attached to a floor. For example, the base support 202 may be mechanically coupled to a support structure 210 that is coupled to the ground. The base support 202 includes a first base portion 212 and a second base portion 214 coupled such that the second base portion 214 is translatable with respect to the first base portion 212 in a linear degree of freedom.

The arm support 204 may be a horizontal member that is mechanically coupled to the base support 202. The arm support 204 includes a first arm portion 218 and a second arm portion 220. The second arm portion 220 is coupled to the first arm portion 218 such that the second arm portion 220 is linearly translatable in a first linear degree of freedom (DOF) with respect to the first arm portion 218.

The display unit 206 may be mechanically coupled to the arm support 204. The display unit 206 may be moveable in a second linear DOF provided by the linear translation of the second base portion 214 and second arm portion 220.

In some embodiments, the display unit 206 includes a display device, e.g., one or more display screens, projectors, or other display devices, that may display digital images. The display unit 206 may include two viewports 223, where the display device is provided behind or included in the viewports. One or more display screens or other display devices may be positioned on the display unit 206 in place of the viewports 223 in some embodiments.

In some embodiments, the display unit 206 displays images of a worksite (e.g., an interior anatomy of a patient in a medical example), captured by an imaging device such as an endoscope. The worksite may alternatively be a virtual representation of a worksite. The images may show captured images or virtual renderings of instruments 122 of the follower device 104 while one or more of these instruments 122 are controlled by the operator via the input devices of the input system 102.

In some embodiments, the display unit 206 is rotationally coupled to the arm support 204 by a tilt member 224. In the illustrated example, the tilt member 224 is coupled at a first end to the second arm portion 220 of the arm support 204 by a rotary coupling configured to provide rotational motion of the tilt member 224 and the display unit 206 about the tilt axis 226 with respect to the second arm portion 220. In some embodiments, the tilt axis 226 is positioned above the display device in the display unit 206.

Each of the various degrees of freedom discussed herein may be passive and require manual manipulation, or be movable by one or more actuators, such as by one or more motors, solenoids, etc. For example, the rotational motion of the tilt member 224 and the display unit 206 about the tilt axis 226 may be driven by one or more actuators, such as by a motor coupled to the tilt member at or near the tilt axis 226.

The display unit 206 may be rotationally coupled to the tilt member 224 and may rotate about a yaw axis 230. For example, this may be lateral or left-right rotation from the point of view of an operator viewing images of the display unit 206 via the viewports 223. In this example, the display unit 206 is coupled to the tilt member by a rotary mechanism, which may be a track mechanism. For example, in some embodiments, the track mechanism includes a curved track 228 that slidably engages a groove member 229 coupled to the tilt member 224, allowing the display unit 206 to rotate about the yaw axis 230 by moving the curved track 228 through a groove of the groove member 229.

The display system 200 may thus provide the display unit 206 with a vertical linear degree of freedom 216, a horizontal linear degree of freedom 222, a rotational (tilt) degree of freedom 227, and a rotational yaw degree of freedom 231. A combination of coordinated movement of components of the display system 200 in these degrees of freedom allow the display unit 206 to be positioned at various positions and orientations in a workspace of the display unit 206. The motion of the display unit 206 in the tilt, horizontal, and vertical degrees of freedom allows the display unit 206 to stay close to, or maintain contact with, the head of the operator when the operator is providing head input through head motion.

The degrees of freedom of the display system 200 allow the display system 200 to provide pivoting motion of the display unit 206 in physical space about a pivot axis that may be positioned in different locations. For example, the display system 200 may provide motion of the display unit 206 in physical space that corresponds to motion of a head of an operator when operating the display system 200. Such a motion may include rotation about a defined neck pivot axis that approximately corresponds to a neck axis of the head of the operator at the neck of the operator. The rotation allows the display unit 206 to be moved in accordance with the head of the operator that is directing movement of the display unit 206. In another example, the motion may include rotation about a defined forehead pivot axis that approximately corresponds to a forehead axis extending through the head of the operator at the forehead when the display unit 206 is oriented, as shown, in a centered yaw rotary position about the yaw axis 230.

Display unit 206 may include one or more input devices that allow an operator to provide input to manipulate the orientation and/or position of the display unit 206 in space, and/or to manipulate other functions or components of the display system 200 and/or a larger system, (e.g., a teleoperated system).

Illustratively, the display unit 206 includes a head input region 242. In some embodiments, the head input region 242 is positioned on a surface of the display unit 206 that is facing the head of the operator during operation of the display unit 206.

The head input region 242 may be shaped to form a headrest which may be in contact with the head of the operator when the operator is providing head input. More specifically, the head input region 242 may be located in a region above the viewports 223 to be in contact with the forehead of the operator while the operator is viewing images through the viewports 223. The display unit 206 may include one or more head input sensors that sense operator head input to the head input region 242 as commands to cause movement of the imaging device, or otherwise cause updating of the view in the images presented to the operator (such as by graphical rendering, digital zooming or panning, etc.). Further, in some embodiments and some instances of operation, the sensed head movement is used to move the display unit 206 to compensate for the head movement. The position of the head of the operator may, thus, remain stationary relative to the viewports 223, even when the operator performs head movements to control the view provided by the imaging device. A proper alignment of the eyes of the operator with the viewports may thus be ensured.

In some embodiments, sensing the operator head input includes sensing a presence or contact by a head of an operator or by a portion of the head (e.g., forehead) with the head input region 242. The one or more head input sensors may include any of a variety of types of sensors, e.g., resistance sensors, capacitive sensors, force sensors, optical sensors, etc.

Continuing with FIG. 2, the orientation and/or position of the display unit 206 may be changed by the display system 200 based on the operator head input to the head input region 242. For example, sensed operator input is provided to a control system (e.g., the control system 140), which controls actuators of the display system 200 to move the second base portion 214 in linear degree of freedom 216, the second arm portion 220 in linear degree of freedom 222, tilt member 224 in rotary degree of freedom 227, and/or display unit 206 in rotary degree of freedom 231, to cause the display unit 206 to be moved as commanded by (e.g., in accordance with) the sensed operator head input. Sensed operator head input may also be used to control other functions of the display system 200 and/or of a larger system (e.g., teleoperated system 100 of FIG. 1). Thus, in some embodiments, the operator may move his or her head to provide input to control the display unit 206 to be moved by the display system 200 in accordance with the motion of the head, thus allowing the display unit 206 to follow motions of the head of the operator and changes in viewing angle.

In some embodiments, images displayed by the display unit 206, and/or other controlled devices, are changed and manipulated based on the sensed motion of the display unit 206. In some embodiments of a display system, the display unit 206 is rotatable about yaw axis 230 in degree of freedom 231 and one or more of the other degrees of freedom 216, 222, and 227 are omitted from the display system 200. For example, the display unit 206 may be rotated about the yaw axis 230 (e.g., by actuator(s) and/or manually by an operator) and the display unit 206 may be manually positioned higher and/or lower (e.g., by actuator(s) and/or manually by an operator), e.g., using the base support 202 or other mechanism, where horizontal degree of freedom 222 and/or tilt degree of freedom 227 are omitted.

Those skilled in the art will appreciate that FIG. 2 merely shows an example for a configuration of a display system. Alternative configurations supporting movement of the display unit 206 based on an input from the operator are also possible. Any linkage that supports the desired movement of the display unit 206 may be used in lieu of the configuration shown in FIG. 2.

Although described herein primarily with respect to the display unit 206 that is part of a grounded mechanical structure (e.g., the display system 200), in other embodiments, the display unit may be any technically feasible display device or devices. For example, the display unit could be a handheld device, such as a tablet device or mobile phone, that is held by an operator. As another example, the display unit could be a head-mounted device (e.g., glasses, goggles, helmets). In such cases, the position and/or orientation of the display unit may be determined using one or more accelerometers, gyroscopes, inertial measurement units, cameras, and/or other sensors internal or external to the display unit.

Imaging Device Control Via Multiple Input Modalities

As described, in some embodiments, a head input device in a display unit can include one or more head input sensors that sense operator head input (e.g., head input that applies forces to, or moves or reconfigures, a display unit such as display unit 206). Similarly, a hand-operated controller can include one or more hand input sensors that sense operator hand input (e.g., hand input that applies forces, or moves or reconfigures, one or more input devices of the hand-operated controller, such as input devices 106). In some embodiments, the sensed head input and the sensed hand input are utilized differently in a first mode and a second mode. In the first mode, sensed input from one input modality is used to determine commands that cause a change in the field of view of an imaging device, or in the portion that is displayed of an image captured by the imaging device. In the second mode, sensed inputs from two input modalities are used together to produce commands that cause a change in the field of view or the portion displayed. In some embodiments, the first mode uses head inputs to determine the commands that cause a change in the field of view of the imaging device, and such a mode is also referred to herein as the "display unit control mode." In some embodiments, the first mode uses hand inputs to determine the commands that cause a change in the field of view of the imaging device, and such a mode is also referred to herein as the "hand-operated control mode." In some embodiments, the second mode uses head and hand inputs together to determine the commands that cause a change in the field of view of the imaging device, and such a mode is also referred to herein as the "combined control mode." Some embodiments have modes in addition to first and second modes, such as third, fourth, or other modes. For example, some embodiments have a first mode that is a "hand-operated control mode" (or a "display unit control mode"), a second mode that is a "combined control mode," and a third mode that is a "display unit control mode" (or "head-operated control mode").

The field of view of the imaging device may be changed through physical movement of the imaging device, internal reconfiguration of imaging elements (e.g. optical elements for an optical sensor) within the imaging device, or digital zooming and panning of the captured image. Changes to the portion of the captured image that is displayed can be achieved through digital zooming or panning, computational interpolation or extrapolation, and the like. Changes to the displayed image can be caused by changes to the field of view that overlap with the portion that is displayed, by digital zooming and panning, or a combination of the foregoing.

As a specific example where the displayed image is the entire captured image, movement of the imaging device changes a view in images captured by the imaging device and presented to the operator via the display unit. For example, head input provided by head forces or movements to the display unit, or hand input provided by hand forces or movements to the hand-operated controller, or a combination of such head and hand inputs, can be captured and converted to commands for moving a repositionable structure to which the imaging device (e.g., within an endoscope assembly) is mounted. The imaging device may be used to capture and provide images of a portion of a worksite that is displayed for output via a display unit of an input system (e.g., the display unit 112 of the input system 102).

Various embodiments utilize approaches for controlling an imaging device, or the portion of the captured image shown to the operator, based on different input modalities, such as the display unit input modality and a hand-operated controller input modality described above. Further, if the follower device supporting the imaging device is unable to follow the commands based on input from multiple input modalities due to range of motion limits (e.g., limits associated with the imaging device and/or a repositionable structure of the follower device to which the imaging device is mounted, obstacles, collisions, and/or the like), various embodiments provide haptic feedback indicative of such limits. Such haptic feedback can help facilitate operator understanding of the limits. An example haptic feedback resists further attempts by the operator to move or otherwise operate a particular input modality in a manner that provides commands that cannot be followed by a follower device.

Figure 3:
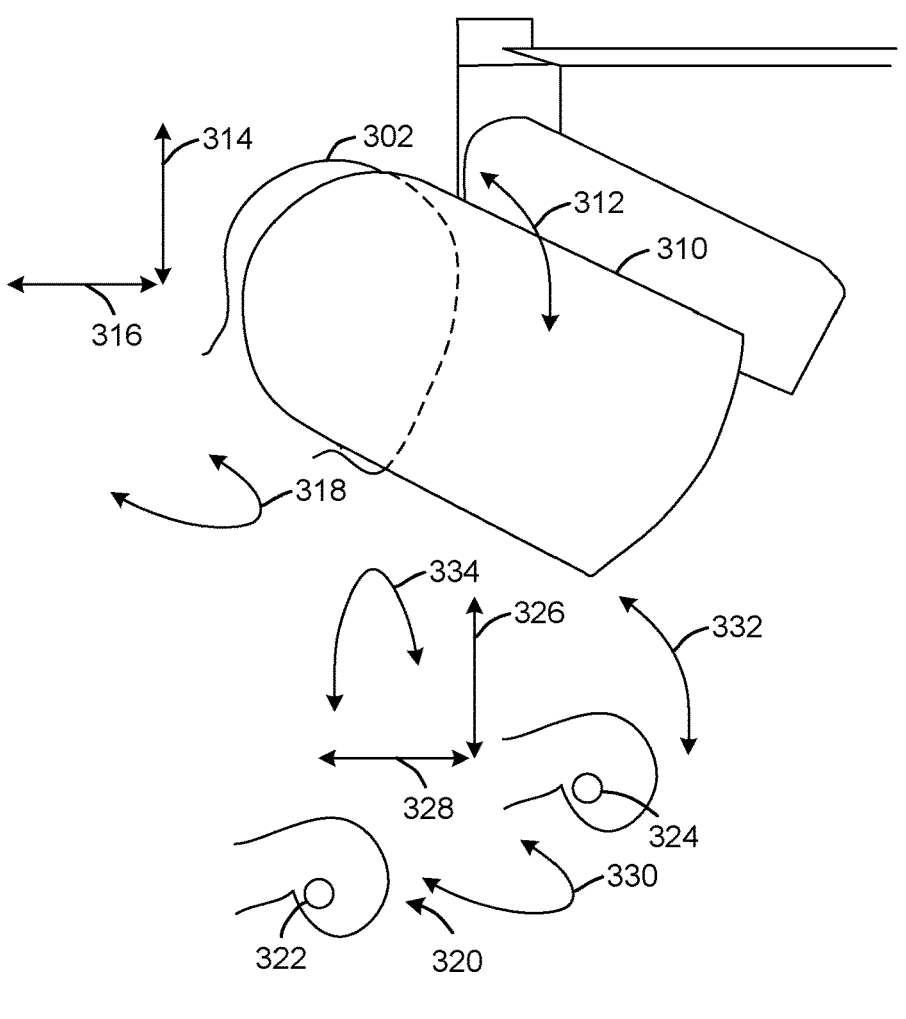
FIG. 3 shows various degrees of freedom of a display unit, a hand-operated controller, and an imaging device, according to various embodiments.
Figure 3:
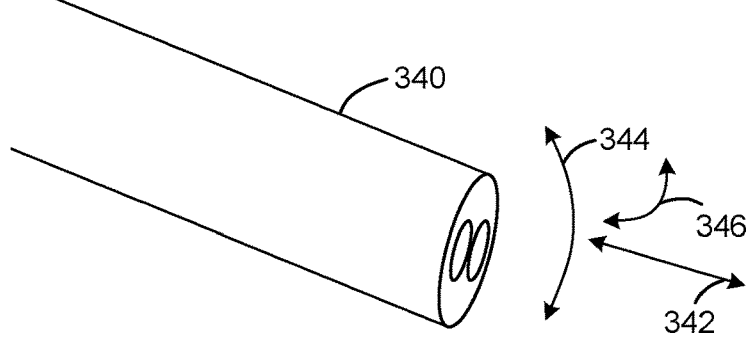

FIG. 3 shows various degrees of freedom of a display unit, a hand-operated controller, and an imaging device, according to various embodiments. As shown in panel A, in some examples, a display unit 310, corresponding to the display unit 112 of FIG. 1 and the display unit 206 of FIG. 2, is movable in four DOFs. In the particular system posture shown in FIG. 3, an operator 302 can translate the display unit 310 in the vertical (up and down on the page) DOF 314, and also the horizontal (left and right on the page) DOF 316. In the particular system posture shown, the operator 302 can also rotate the display unit 310 about a vertical axis (yaw) DOF 318 and rotate the display unit 310 about a horizontal axis (pitch) DOF 312. For example, as described above in conjunction with FIG. 2, the orientation and/or position of the display unit 206 may be changed based on operator head input to head input region 242 to manually move the display unit 206, or to control actuators of the display system 200 to move the display unit 206. For example, the manual or actuator-provided movement can follow the movement of the head of an operator by moving the second base portion 214 in linear degree of freedom 216, the second arm portion 220 in linear degree of freedom 222, the tilt member 224 in rotary degree of freedom 227, and/or the display unit 206 in rotary degree of freedom 231.

As also shown, a hand-operated controller 320 includes input devices 322, 324 that can be manipulated by the hands of the operator 302 and moved in any technically feasible number of DOFs. In some embodiments, the hand-operated controller has six DOFs (translation along, and rotation about, three axis). In other embodiments, the hand-operated controller may have fewer than six DOFs, or more than six DOFs (e.g. through internal configuration changes). Illustratively, the hand-operated controller 320 includes two hand-operated input devices 322, 324, corresponding to the input devices 106 described above in conjunction with FIG. 1, that can be manipulated jointly. In addition, hand input from the hand-operated input devices 322, 324 can be processed as a simulated handlebar control. Although a hand-operated controller 320 with two input devices 322, 324 is shown for illustrative purposes, any technically feasible hand-operator controller with any number or type of input devices may be used in some embodiments. For example, in some embodiments, the hand-operated controller may include a single input device in the form of a single handlebar manipulated by the hands of an operator. As another example, in some embodiments, the hand-operated controller may include a single input device that is manipulated by one hand of an operator, or two or more input devices among which the operator holds a subset at a time, etc. As yet another example, the hand-operated controller 320 may include grounded or ungrounded input devices. In the example and system posture shown, the hand-operated controller 320 includes input devices 322, 324 that each can be translated in a vertical (up and down on the page) DOF 326, translated in a first horizontal (left and right on the page) DOF 328, and can be rotated about a vertical axis in a yaw DOF 330, and rotated about the second horizontal axis in a pitch DOF 332. In some embodiments, the input devices 322, 324 can also be translated in a second horizontal (in and out of the page) DOF (not shown) and rotated about the first horizontal axis in a roll DOF (not shown). In addition, the hand-operated controller 320 can be moved in coordination in a multi-input device rotation DOF 334 that orbits (rolls) about a midpoint between the input devices 322, 324. In other embodiments, the hand-operated controller 320 may contain input devices that are moveable in more or fewer DOFs. For example, in some embodiments, the input devices 322, 324 can also be reconfigured internally in additional DOFs (not shown) and adopt different shapes. As another example, in some embodiments, the input devices 322, 324 can have only a subset of the three translational and three rotational DOFs for a rigid body in free space.

Although described herein primarily with respect to embodiments that include two input modalities (e.g., a display unit input modality and a hand-operated controller input modality), other embodiments may include more than two input modalities. For example, additional input modalities may be provided by additional display units that are also input devices, additional hand-operated controllers, one or more foot-operated controllers, one or more arm controllers, and etc.

As shown in panel B, an imaging device 340, when mounted on a manipulator arm 120 that comprises a repositionable structure and being operated by the operator 302, may be limited to move in three DOFs. In some examples, the imaging device 340 may be introduced into a worksite through an access port or cannula. In an example of such cases, the imaging device 340 may have a pitch DOF 344, a yaw DOF 346, and an insertion-retraction DOF 342 about a remote center of motion associated with the access port or cannula. For example, the imaging device 340 could be a 0° endoscope, in which case a direction of view of the imaging device 340 corresponds to the insertion direction of the insertion-retraction DOF 342. As another example, the imaging device could be a 30° (or other offset) endoscope, in which case the direction of view of the imaging device 340 would have a 30° deviation (or other rotational deviation) from the insertion direction of the insertion-retraction DOF 342. In addition, an endoscope may also have a roll DOF for rotation about the shaft of the endoscope, one or more joints along the endoscope shaft that provides additional DOFs, etc.

Figure 4:
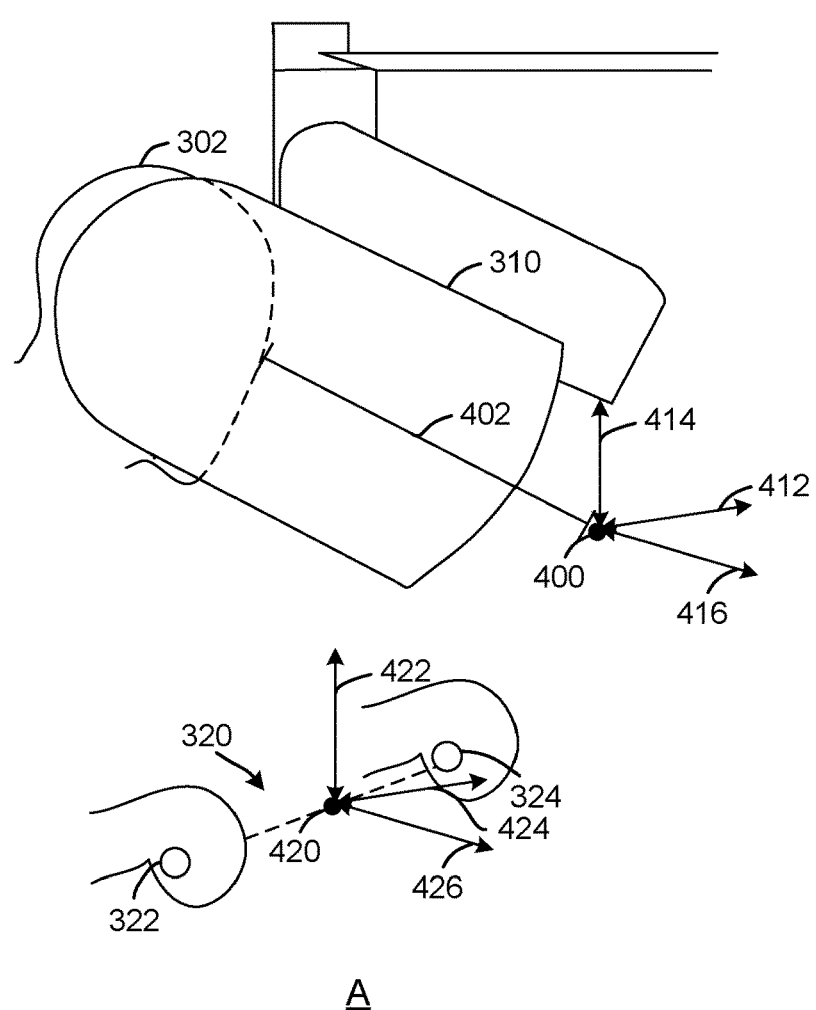
FIG. 4 illustrates example reference points in a display unit workspace, a hand-operated controller workspace, and an imaging device workspace, according to various embodiments.
Figure 4:
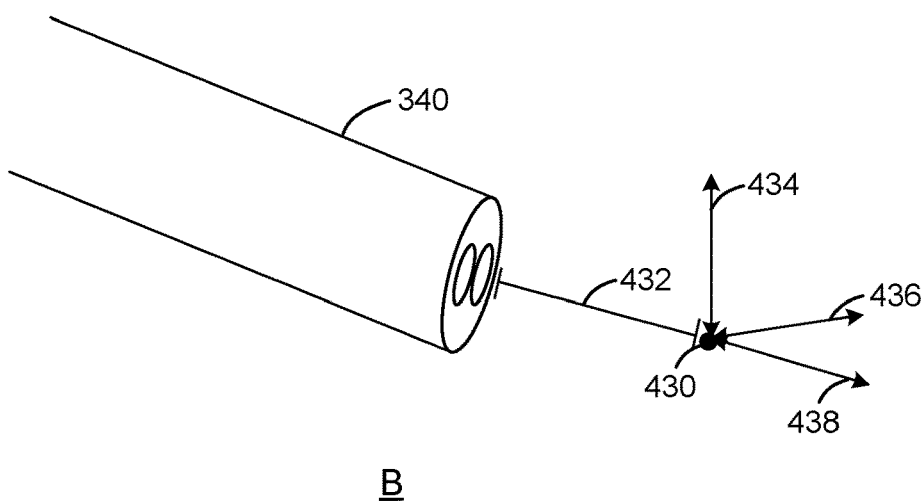

FIG. 4 illustrates example reference points in a display unit workspace, a hand-operated controller workspace, and an imaging device workspace, according to various embodiments. Panels 4A-B further illustrate mapping motion of the display unit 310 and motion of the hand-operated controller 320 to commanded motion of the imaging device 340, using a control system (e.g., the control system 140), by determining a target position for a reference point 430 (also referred to herein as the "imaging device reference point 430"). The imaging device reference point 430 is offset from the imaging device 340. The target position is determined based on the position of a reference point 400 (also referred to herein as the "display unit reference point 400") and the position of a reference point 420 (also referred to herein as the "hand-operated controller reference point 420"). In some embodiments, the reference point 420 is a position referenced to the input devices 322, 324 of the hand-operated controller 320; for example, reference point 420 may be defined based on the location, orientation, and/or physical configuration of the hand-operated controller 320. In the FIG. 4 example, the hand-operated reference point 420 is at a midpoint between the input devices 322, 324. As shown, the display unit reference point 400 is offset from the display unit 310 by being a distance "in front of" the display unit 310 in a direction away from the eyes of the operator 302 when viewing images on the display unit, and in other embodiments the offset may be in another direction. The imaging device reference point 430 is offset from the imaging device 340 by being a distance "in front of" the imaging device 340 in the direction of the field of view of the imaging device. In other embodiments, the offset may be in another direction.

The control system can regularly determine and update the target position as the current position of the display unit reference point 400, and/or the current position of the hand-operated controller reference point 420, is changed. The target position can be determined such that motion of the imaging device reference point 430 toward the target position would be similar to a combination of a motion of the display unit reference point 400 from a previous position to a current position and a motion of the hand-operator controller reference point 420 from a previous position to the current position. The combination may be a straight sum, a weighted sum, a time-averaged sum, a linear or nonlinear combination, or any other appropriate combination of the motions of the display unit reference point 400 and hand-operator controller reference point 420. A reference point 400, 420 that does not move between the previous and current positions can have zero contribution to the combination. As a result, using the display unit reference point 400, the hand-operator controller reference point 420, and the imaging device reference point 430, operator input that changes the position of the display unit 310 and/or the position of the hand-operator controller 320 can be mapped to commanded positions, velocities, and/or accelerations of the imaging device 340.

In some examples, the display unit reference point 400 is located at a distance 402 in front of lenses (e.g., lenses of the viewports 223 of the display unit 206) of the display unit 310 in a direction away from the operator 302, i.e., in front of eyes of the operator 302 when looking through the viewports 223. In some examples, the display unit reference point 400 may be approximately 30 cm in front of the lenses of the display unit 310 in the direction away from the operator 302, which is roughly the distance between the eyes and the hands of an operator 302 of average stature. In some examples, such as in cases where the display unit 310 is an ungrounded, head-mounted device, the display unit reference point 400 may still be approximately 30 cm in front of the head-mounted device, or where the eyes of the operator would be when viewing through the head-mounted device.

In some examples where the system utilizes two or more input devices for the hand-operated controller reference point 420, the hand-operated controller reference point 420 may be located at a center of mass, center of geometry, or other physically-defined reference location of the input devices. For example, in some examples where the system utilizes two input devices 322, 324 for providing the hand-operated controller reference point 420, the hand-operated controller reference point 420 can be located at a midpoint or other geometric reference location between the input devices 322, 324. In other embodiments in which the system utilizes a single input device for the hand-operated controller reference point 420, the hand-operated controller reference point 420 may be located at a predefined location of the input device, a predefined location of the hand operating the input device, a location at one hand of an operator, etc.

In some examples, including some cases where the display unit reference point 400 is approximately 30 cm in front of the eyes of the operator, the imaging device reference point 430 may be set at a distance in front of a distal end of the imaging device 340 that is roughly the expected distance between the imaging device 340 and one or more teleoperated instruments (e.g., the instrument 122 of the follower device 104) during use at the worksite (e.g., in some cases, at a fixed distance of approximately 10 cm). In some embodiments, the distance of the display unit reference point 400 in front of the operator 302 and/or the distance of the imaging device reference point 430 in front of the imaging device 340 is not fixed, and may vary with operator configuration, digital and/or optical zoom being applied, system mode, operating conditions, types of instruments 122 being used, procedure being performed, etc. For example, images captured by the imaging device 340 and presented to an operator via the display unit 310 may be modified by optical or digital zooming or panning of the imaging device 340 and/or optical zooming or panning applied to an image displayed by the display unit 310. In such cases, the imaging device reference point 430 can be moved relative to the imaging device 340 based on the optical or digital zooming and panning, even though the imaging device 340 itself has not moved. For example, physical (e.g. optical) or digital zooming out and in could move the imaging device reference point 430 along a central axis of a field of view and further away or closer relative to the imaging device 340, while optical or digital panning could move the imaging device reference point 430 off of a central axis of the field of view and laterally relative to the imaging device 340.

As shown, the position of the display unit reference point 400 can be represented in any appropriate coordinate system, such as with Cartesian coordinates $(x_d, y_d, z_d)$, which are shown as the axes 412, 414, and 416. Similarly, the position of the hand-operated controller reference point 420 can be represented in Cartesian coordinates $(x_h, y_h, z_h)$, which are shown as the axes 422, 424, and 426. The position of the image device reference point 430 can also be represented in Cartesian coordinates $(x_i, y_i, z_i)$, which are shown as the axes 434, 436, and 438. Irrespective of the DOFs of the display unit 310, described above in conjunction with FIG. 3, movement of the display unit 310 in any of the DOFs of display unit 310 may be projected in front of the display unit 310 by the distance 402 to determine the display unit reference point 400 in terms of $x_d$, $y_d$, and $z_d$. A similar mapping may also be used to determine the relationship between movement of the imaging device 340 in any of the DOFs of imaging device 340 and movement of the imaging device reference point 430 in $x_d$, $y_d$, and $z_d$ coordinates (or another coordinate system). In addition, to determine the hand-operated controller reference point 420 in $x_h$, $y_h$, and $z_h$ coordinates (or another coordinate system), a physical reference such as a midpoint between the input devices 322, 324 may be computed; this hand-operated controller reference point 420 thus follows movements of the input devices 322, 324.

In some embodiments, the control system solves for the positions of the display unit reference point 400 and the hand-operated controller reference point 420 using forward kinematics and known joint positions of repositionable structures supporting the display unit 310 and the input devices 322, 324, respectively. For example, the control system could itself compute the joint positions for following the head motions of the operator 302, or obtain those joint positions from another module that computes the joint positions, solve for the position of the lenses of the display unit 310 based on the joint positions via forward kinematics, and add the distance 402 in front of the position of the lenses in a direction perpendicular to the view plane of the lenses to determine the position of the display unit reference point 400. In addition, the control system could itself compute the joint positions subsequent to movement of the input devices 322, 324 by the hands of the operator, or obtain those joint positions from another module that computes the joint positions, solve for the midpoint or other reference position between the input devices 322, 324 via forward kinematics to determine the position of the hand-operated controller reference point 420. In other embodiments, the control system can determine the positions of the display unit reference point 400 and the hand-operated controller reference point 420 in any technically feasible manner. For example, when the display unit is an ungrounded head-mounted display, a point representing the position of the display unit could be tracked using data captured by sensors in or physically coupled to the head-mounted display and/or using one or more sensors external to the head-mounted display. A distance can then be added to the position of the display unit to obtain the position of the display unit reference point 400. Similarly, in some examples, positions of one or more input devices of a hand-operated controller may be determined using sensors in or physically coupled with the one or more input devices and/or using one or more sensors external to the input device(s), and the hand-operated controller reference point 420 computed based on the positions of the one or more input devices.

In some embodiments, after determining the position of the display unit reference point 400 and the position of the hand-operated controller reference point 420, the control system generates control command(s) based on a combination of the change in the position of the display unit reference point 400 and the change in the position of the hand-operated controller reference point 420. The combination of the change in the position of the display unit reference point 400 and the change in the position of the hand-operated controller reference point 420 is then used to determine a change in position of a target position for the imaging device reference point 430. The control system then sends the control command(s) as input(s) to a repositionable structure to which the imaging device 340 is mounted, thereby causing the repositionable structure to move such that the imaging device reference point 430 moves toward the target position of the imaging device reference point 430. The display unit reference point 400 and the hand-operated controller reference point 420 can be combined using a straight sum, a weighted sum, a time-averaged sum, a linear or nonlinear combination, or any other appropriate combination to determine the target position. In some embodiments, the target position may be defined with a scaling factor being applied. As described in greater detail below, the same or different scaling factors can be applied to motions of the display unit reference point 400 and to motions of the hand-operated controller reference point 420, and the scaled motions of the display unit reference point 400 and the hand-operated controller reference point 420 can be combined to obtain corresponding target positions for the imaging device reference point 430. For example, Cartesian motion of the display unit reference point 400 along the $x_d$, $y_d$, and $z_d$ degrees of freedom and of the hand-operated controller reference point 420 along the $x_h$, $y_h$, and $z_h$ degrees of freedom can be mapped to corresponding target positions subject to the scaling factor(s). In some examples, the scaling factor(s) may be determined based on operator preference, a type of the display unit 310, a type of the hand-operated controller 320, a type of the imaging device 340, a procedure being performed, and/or the like.

In some embodiments, the repositionable structure to which the imaging device 340 is mounted may be actuated to update a position and/or orientation of the imaging device 340 at the worksite so that the imaging device reference point 430 moves to, or toward, the target position. In such cases, the control system can use the target position of the imaging device reference point 430 to determine the position of the distal end of the imaging device 340, as described in greater detail below in conjunction with FIG. 5. The inverse kinematics for the imaging device 340 and/or the repositionable structure to which the imaging device 340 is mounted can then be used to determine how to actuate the joints of the imaging device 340, and/or the joints of the repositionable structure to which the imaging device 340 is mounted, to move the imaging device 340 accordingly.

In some embodiments, one or more instruments (e.g., one or more of the instruments 122) are moved relative to a reference frame that does not change when the imaging device 340 moves. For example, in the follower mode described above, the one or more instruments could be moved relative to the reference frame based on commands generated using inputs from the hand-operated controller 320. In such a case, when the imaging device 340 is moved, the different views of an environment enabled by movement of the imaging device 340 does not affect the reference frame in which instruments are controlled. The different views of the environment only change the field of view of the imaging device 340 relative to the instruments, which changes an effective point of view presented by images captured by the imaging device 340 to an operator of the instruments.

Figure 5:
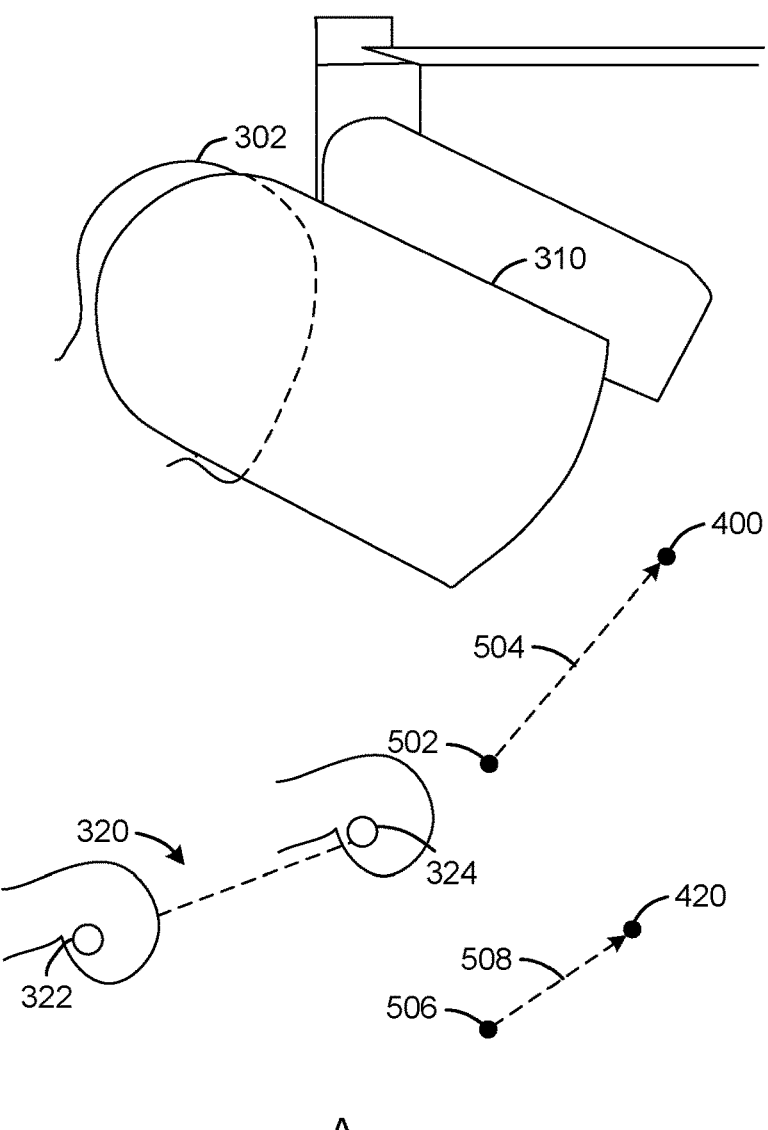
FIG. 5 illustrates a mapping between changes to the reference points in display unit and hand-operated controller workspaces and changes to the reference point in the imaging device workspace, according to various embodiments.

FIG. 5 illustrates a mapping between changes to the reference points in display unit and hand-operated controller workspaces and changes to the reference point in the imaging device workspace, according to various embodiments. As shown, in some examples, the position of the display unit reference point 400 is defined relative to the position of a display unit baseline reference point 502, the position of the hand-operated controller reference point 420 is defined relative to the position of a hand-operated controller baseline reference point 506, and the position of the imaging device reference point 430 is defined relative to the position of an imaging device baseline reference point 510. The imaging device baseline reference point 510 may be defined based on the posture of the display unit 310 at the time when the operator 302 selects to enter a display unit control mode or a combined control mode. For example, the display unit baseline reference point 502 could be defined as a point at a certain distance in front of the display unit 310 in a direction away from the operator 302 when the operator 302 selects to enter the display unit control mode. In the display unit control mode, movement of the display unit 310 is converted to commands to cause movement of the imaging device 340 to follow the movement of the display unit 310. In the combined control mode, movement of the display unit 310 is combined with input to the hand-operated controller to cause movement of the imaging device 340. The position of the display unit reference point 400 at a subsequent time can then be represented as a delta 504, denoted herein by $\Delta^{display\ unit}$, between the current display unit reference point 400 and the display unit baseline reference point 502.

The hand-operated controller baseline reference point 506 may be defined based on the posture of the input device(s) (e.g. input devices 322, 324) at the time when the operator 302 selects to enter a hand-operated control mode or the combined control mode. For example, the hand-operated controller baseline reference point 506 may be defined as a midpoint between the input devices 322, 324 of the hand-operated controller 320 when the operator 302 selects to enter the hand-operated control mode or the combined control mode. In the hand-operated control mode, movement of one or more input devices of the hand-operated controller 320 is converted to commands to cause movement of the imaging device 340 to follow the movement of the hand-operated controller 320. The hand-operated controller reference point 420 at a subsequent time can be represented as a delta 504, denoted herein by $\Delta^{hand\text{-}operated}$ between the current hand-operated controller reference point 420 and the hand-operated controller baseline reference point 506.

The imaging device baseline reference point 510 may be defined as a point at a certain distance in front of the imaging device 340 away from the operator 302 when the operator 302 selects to enter either the display unit control mode, the hand-operated control mode, or the combined control mode. The position of the imaging device reference point 430 at a subsequent time can then represented as a delta, denoted herein by $\Delta^{image\ device}$, between the current imaging device reference point and the imaging device baseline reference point 510.

In some embodiments, changes in position of the display unit reference point 400 and of the hand-operated controller reference point 420 can be mapped to changes in position of the imaging device reference point 430 by applying scaling factors according to Equation 1.

$$\Delta^{imaging\ device}=\text{scaling}^{hand\text{-}operated}\times\Delta^{hand\text{-}operated}+$$
$$\text{scaling}^{display\ unit}\times\Delta^{display\ unit} \qquad \text{Equation 1}$$

In Equation 1, the scaling factors $\text{scaling}^{hand\text{-}operated}$ and $\text{scaling}^{display\ unit}$ can be, for example, static or variable, or be equal or different in value from each other. As a specific example, the scaling factors can be selectable, discrete values, such as less than one (e.g., $\frac{1}{3}$, $\frac{1}{2}$, $\frac{2}{3}$) for finer control of the imaging device 340, equal to one for general control of the imaging device 340, and greater than one (e.g., 1.5, 2, 3) for coarser control of the imaging device 340. Equation 1 assumes that both the hand-operated control mode and the display unit control mode have been entered, i.e., the control system is in a hand-operated plus display unit control mode. It should be understood, however, that the operator may enter only the hand-operated control mode or the display unit control mode, in which case changes in position of the imaging device reference point 430 may be determined by scaling changes in position of the hand-operated controller reference point 420 or scaling changes in position of the display unit reference point 400, respectively, i.e., the delta for an unused control mode is zero.

In some cases, the imaging device reference point 430 may be unable to follow the display unit reference point 400 and the hand-operated controller reference point 420 according to Equation 1 due to, for example, range of motion (ROM) limits associated with the imaging device 340 and/or the repositionable structure to which the imaging device 340 is mounted, obstacles, collisions, and/or the like. The ROM limits may be physically imposed (such as due to physical joint limits), software-imposed, or a combination where some ROM limits are physically and software-imposed. In such cases, the control system may determine and provide haptic feedback to the input devices 322, 324 of the hand-operated controller 320 and/or to the display unit 310. As described, a particular input modality (e.g., the hand-operated controller 320 or the display unit 310) that caused the inability to follow can be identified to provide haptic feedback that resists further attempts by the operator 302 to move that input modality in a manner that cannot be followed by the imaging device 340. As shown, in some examples, the control system determines, using two virtual follower devices 520 and 530, whether input from the hand-operated controller 320 or the display unit 310 caused ROM limits associated with the imaging device 340 to be exceeded.

Each of the virtual follower devices 520 and 530 is used to simulate movements of the imaging device 340 and is associated with virtual ROM limits corresponding to actual ROM limits of the imaging device 340 and/or the repositionable structure on which the imaging device 340 is mounted. The virtual follower devices 520 and 530 are used to prevent commanded positions for a repositionable structure on which the imaging device 340 is mounted from exceeding ROM limits of the repositionable structure. In some embodiments, to determine whether the ROM limits are exceeded, the control system uses inverse kinematics to compute resulting joint positions of the repositionable structure, sends commanded positions as inputs to the virtual follower devices 520 and 530, and compares those joint positions with predefined joint limits, i.e., the virtual ROM limits.

In some embodiments, the control system verifies whether a position of the first virtual follower device 520 that is associated with a first virtual target position 514, violates the virtual ROM limits associated with the first virtual follower device 520. In this example, the first virtual target position 514 is determined based on the hand-operated controller reference point 420 according to Equation 2, $$\Delta^{virtual\ follower}=\text{scaling}^{hand\text{-}operated}\times\Delta^{hand\text{-}operated} \qquad \text{Equation 2}$$

In Equation 2, $\Delta^{virtual\ follower}$ is a delta, shown as delta 512, between virtual target position 514 in front of the first virtual follower device 520 and the imaging device baseline reference point 510. When the first virtual target position 514 cannot be achieved due to virtual ROM limits associated with the first virtual follower device 520, the control system provides haptic feedback to the input devices 322, 324 of the hand-operator controller 320 to constrain motion of the input devices 322, 324 so that there is no (or reduced) lost motion between the hand-operated controller 320 and the imaging device 340. In some embodiments, the haptic feedback is proportional to a difference between a delta of the imaging device reference point 430 that is achievable, determined using the first virtual follower device 520 and denoted herein by $\Delta^{virtual\ follower\ achievable}$, and a delta associated with the position of the first virtual target position 514 by applying a scaling factor, according to Equation 3.

$$F_{fbk}=\alpha^{hand\text{-}operated}\times(\Delta^{first\ virtual\ follower\ achievable}-\text{scaling}^{hand\text{-}operated}\times\Delta^{hand\text{-}operated}) \qquad \text{Equation 3}$$

In Equation 3, $F_{fbk}$ is the haptic feedback applied to the input devices 322, 324 of the hand-operated controller 320, and $\alpha^{hand\text{-}operated}$ is a proportionality constant. The control system can further convert the haptic feedback to joint forces and/or torques for joints of repositionable structure(s) to which the input devices 322, 324 are mounted. In some examples, the haptic feedback may be determined and/or applied separately for each of the $x_d$, $y_d$, and $z_d$ axes of the hand-operated controller reference point 420.

As shown, the control system also verifies whether a second virtual target position 518 of the second virtual follower device 530, determined according to Equation 1, violates the virtual ROM limits associated with the second virtual follower device 530. When the target position of the second virtual follower device 530 violates the virtual ROM limits, the control system provides haptic feedback to the display unit 310 to constrain motion of the display unit 310 so that there is no (or reduced) lost motion between the display unit 310 and the imaging device 340. In some embodiments, the haptic feedback is proportional to a difference between a delta associated with a position of the imaging device reference point 430 that can be achieved, determined using the second virtual follower device 530, and a delta (shown as the delta 516) associated with the position of the second virtual target position 518 by applying a scaling factor, according to Equation 4.

$$F_{fbk} = \alpha^{display\ unit} \times (\Delta^{second\ virtual\ follower\ achievable} - \Delta^{first\ virtual\ follower\ achievable} - scaling^{display\ unit} \times \Delta^{display\ unit})$$

Equation 4

In Equation 4, $F_{fbk}$ is the haptic feedback applied to the display unit 310, $\alpha^{display\ unit}$ is a proportionality constant, the delta $\Delta^{second\ virtual\ follower\ achievable}$ is an achievable position of the imaging device reference point 430 determined using the second virtual follower device, and the delta $\Delta^{first\ virtual\ follower\ achievable}$ is an achievable position of the imaging device reference point 430 determined using the first virtual follower device. The control system can further convert the haptic feedback to joint forces and/or torques for joints of a repositionable structure to which the display unit 310 is mounted. In some examples, the haptic feedback may be determined and/or applied separately for each of the $x_d$, $y_d$, and $z_d$ axes of the display unit reference point 400.

In some embodiments, the control system also causes haptic feedback to be provided through the input devices 322, 324. The haptic feedback may be based on a deviation of the actual position achieved by the imaging reference point 430 from a target position, such as a target position determined using the virtual follower devices 520 and 530 described above, when the imaging device 340 is commanded to move based on the target position. In some embodiments, the control system determines a difference between an actual position achieved by the imaging device reference point 430 and the target position. Then, the control module provides haptic feedback to the input devices 322, 324 of the hand-operated controller 320 by applying a scaling factor, according to Equation 5. As an alternative, the difference between the actual position achieved by the imaging device 340 itself and a commanded position of the imaging device 340 can be used.

$$F_{fbk} = \alpha^{actual} \times (actual\ position - target\ position)$$

Equation 5

In Equation 5, $F_{fbk}$ is the actual haptic feedback applied to the input devices 322, 324 of the hand-operated controller 320, and $\alpha^{achieved}$ is a proportionality constant. In some examples, haptic feedback is not provided. For example, in some examples, haptic feedback is not provided to the display unit 310 when the actual position achieved by the imaging device 340 is different from a command position of the imaging device 340. Haptic feedback may not be provided for a variety of reasons, including cost savings, reduced system complexity, reduced operator discomfort, etc.

Further, in some embodiments, the control system accounts for motion of the display unit 310, motion of the input devices (e.g. 322, 324) of the hand-operated controller 320, that does not result in motion of the imaging device 340, or for motion of the imaging device 340 that does not result from commands from display unit 310, the input device 322, 324, or some other component of the input system 102. For example, such unlinked motion may result from manual adjustments to the position or orientation of: the display unit 310, the input devices 322, 324, and/or the imaging device 340. For example, the operator 302 could make an ergonomic adjustment to the position or orientation of the display unit 310, or the input devices 322, 324 of the hand-operated controller 320. Specifically, in a first example, the operator 302 could exit the display unit control mode, manually adjust the position or orientation of display unit 310, and then re-enter the display unit control mode. In a second example, the operator 302 could exit the hand-operated control mode, manually adjust the position or orientation of the input devices 322, 324, and then re-enter the hand-operated control mode. In such cases, the position or orientation of the display unit 310 or the input devices 322, 324 could be manually changed (e.g., for any reason including operator ergonomics), but the control system does not command a movement of the imaging device 340 to follow the movement associated with that adjustment. As another example, the imaging device 340 could be manually adjusted if the operator 302 or other personnel or something else moved the imaging device 340. Specifically, in an example, the operator 302 could exit the display unit control mode, the hand-operated control mode, and/or the combined control mode, manually adjust the imaging device 340, and then re-enter the display unit control mode or the hand-operated control mode. In such a case, the position of the imaging device 340 is displaced, but the positions of the display unit 310 and the input devices 322, 324 of the hand-operated controller 320 do not change.

As described in greater detail below, in some embodiments, when the position or orientation of the display unit 310 is adjusted in an ergonomic adjustment mode, in which no corresponding command is issued to move the imaging device 340, the control system: (1) updates the display unit baseline reference point 502 based on a position and orientation of the display unit 310 at or until a completion of the change in position or orientation (which sets the delta 504 of the display unit reference point 400 to zero), and (2) solves for the correction in Equation 6. In some embodiments, the control system then (3) performs a ratcheting technique to reduce the correction over a number of movement cycles.

$$\Delta^{imaging\ device} = scaling^{hand-operated} \times \Delta^{hand-operated} + scaling^{display\ unit} \times \Delta^{display\ unit} + correction$$

Equation 6

Similarly, in some embodiments, when the position or orientation of one or more of the input devices (e.g., the input devices 322, 324) of the hand-operated controller 320 is adjusted in an ergonomic adjustment mode, in which no corresponding command to move the imaging device 340 is issued, the control system (1) updates the hand-operated controller baseline reference point 506 based on the positions and orientations of the one or more input devices at or until a completion of the ergonomic adjustment (which sets the delta 508 of the hand-operated controller reference point 420 to zero). The control system then (2) solves for the correction in Equation 6. In some embodiments, the control system further (3) performs a ratcheting technique to reduce the correction over a number of movement cycles.

Further, in some embodiments, when the position or orientation of the imaging device 340 adjust moved without command(s) that are generated based on input(s) from the display unit 310, the input device 322, 324, or some other component of the input system 102, the control system: (1) updates the imaging device baseline reference point 510 based on a position and orientation of the imaging device 340 at a completion of the change in position or orientation (which sets the delta of the imaging device reference point 430 to zero), and (2) solves for the correction in Equation 6. In some embodiments, the control system then (3) performs a ratcheting technique to reduce the correction over a number of movement cycles.

In other embodiments that include more than two input modalities, changes in the position of one or more reference points associated with each of the input modalities may be scaled and combined to provide a target position for the imaging device reference point. The combination may be a simple sum, a weighted sum, linear or nonlinear, or any other appropriate combination. In addition, one virtual follower device may be used to determine, for each of the input modalities, whether the changes in position of each of the reference point(s) associated with that input modality causes associated virtual ROM limits to be violated. In some embodiments, violation of the ROM limits leads to provision of haptic feedback for that input modality.

Figure 6B:
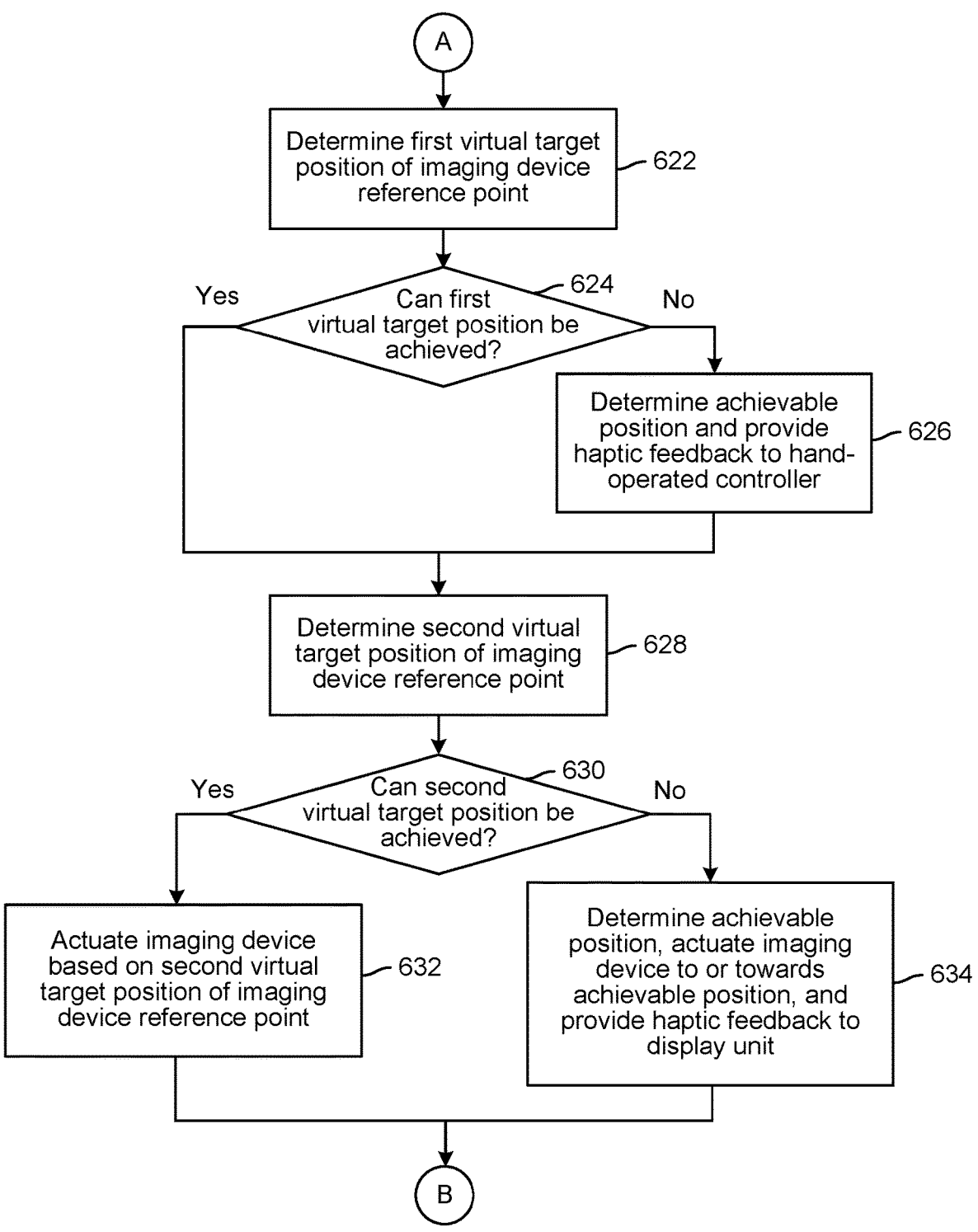

FIGS. 6A-6B illustrate a simplified diagram of a method 600 for controlling an imaging device, according to various embodiments. One or more of the processes 602-634 of method 600 may be implemented, at least in part, in the form of executable code stored on non-transitory, tangible, machine readable media that when run by one or more processors (e.g., the processor 150 in control system 140) may cause the one or more processors to perform one or more of the processes 602-634. In some embodiments, method 600 may be performed by one or more modules, such as control module 170 in the control system 140. In some embodiments, method 600 may include additional processes, which are not shown. In some embodiments, one or more of the processes 602-634 may be performed, at least in part, by one or more of the units of control system 140.

As shown, method 600 begins at process 602, where the hand-operated controller baseline reference point 506, the display unit baseline reference point 502, and the imaging device baseline reference point 510 are initialized. As described, in some embodiments, the hand-operated controller baseline reference point 506 is a position referenced to the input devices 322, 324 of the hand-operated controller 320; for example, hand-operated controller baseline reference point 506 could be defined based on the position, orientation, and/or physical configuration of the hand-operated controller 320. In some examples, the hand-operated controller baseline reference point 506 is a midpoint between the input devices 322, 324 when a hand-operated control mode is entered. In addition, in some embodiments, the display unit baseline reference point 502 is a position of the display unit reference point 400 when a display unit control mode is entered. The hand-operated controller baseline reference point 506 may be a point in a hand-operated controller reference frame or a world reference frame. Further, in some embodiments, the imaging device baseline reference point 510 is a position of the imaging device reference point 430 when either the hand-operated control mode or the display unit control mode is entered. The imaging device baseline reference point 510 may be a point in a display unit reference frame or a world reference frame.

At process 604, a difference between an actual position of the imaging device 340 and a previously commanded position of the imaging device 340 is determined. For example, the previously commanded position could be a commanded position sent by the control system to a repositionable structure on which the imaging device 340 is mounted during a previous movement cycle. However, the imaging device 340 may fail to achieve such a commanded position due to ROM limits associated with the imaging device 340 and/or the repositionable structure to which the imaging device 340 is mounted, obstacles, collisions, and/or the like. The control system determines, at process 604, a difference between the actual position and the previously commanded position, if any.

At process 606, haptic feedback is provided to the hand-operated controller 320 based on the difference determined at process 604. Where the difference is zero or null, or below some threshold amount, no haptic feedback indicative of the difference may be applied. As described, in some embodiments, the haptic feedback is proportional to a difference between an actual position of the imaging device reference point 430 and a target position of the imaging device reference point 430 associated with the previously commanded position of the imaging device 340. For example, the haptic feedback could be determined according to Equation 5.

At process 608, a position of the hand-operated controller reference point 420 and a position of the display unit reference point 400 are determined. In some embodiments, the position of the hand-operated controller reference point 420 is determined relative to the hand-operated controller, such as a midpoint between the input devices 322, 324, and the position of the display unit reference point 400 is determined at a distance offset from the display unit 310, such as in a direction away from an operator. In some examples, the positions of the hand-operated controller reference point 420 and the display unit reference point 400 can be determined using forward kinematics based on the joint positions of repositionable structures to which the input devices 322, 324 and the display unit 310 are mounted, respectively. In other examples, the positions of the hand-operated controller reference point 420 and the display unit reference point 400 can be determined in any technically feasible manner, such as through one or more sensors in or coupled to the input devices 322, 324 and the display unit 310 and/or using one or more external tracking systems.

At process 610, if the hand-operated controller 420 has been adjusted in a mode where the movement of the hand-operated controller does not cause a corresponding movement of the imaging device 340, then at process 612, the hand-operated controller baseline reference point 506 is updated and a correction is determined. For example, the hand-operated controller 320 could be moved without a corresponding movement of the imaging device 340 when the operator 302 makes a manual adjustment, such as an ergonomic adjustment, to the positions of one or both of the input devices 322, 324. In such cases, the hand-operated controller baseline reference point 506 can be updated by setting the hand-operated controller baseline reference point 506 to the position of the hand-operated controller reference point 420 at a completion of the manual adjustment to the input devices 322 and/or the input device 324.

At process 614, if the display unit 310 has been adjusted in a mode where the movement of the display unit 310 does not cause a corresponding movement of the imaging device 340, then at process 616, the display unit baseline reference point 502 is updated and a correction is determined. For example, the display unit 310 could be moved without a corresponding movement of the imaging device 340 when the operator 302 makes a manual adjustment, such as an ergonomic adjustment, to the display unit 310. In such cases, the hand-operated controller baseline reference point 506 can be updated by setting the display unit baseline reference point 502 to the position of the display unit reference point 400 at a completion of the manual adjustment to the display unit 310.

At process 618, if the imaging device 340 has been moved without command(s) that are generated based on input(s) from the display unit 310, the input device 322, 324, or some other component of the input system 102, then at process 620, the imaging device baseline reference point 510 is updated and a correction is determined. In some embodiments, the hand-operated controller baseline reference point 506 can be updated by setting the hand-operated controller baseline reference point 506 to the position of the hand-operated controller baseline reference point 506 at a completion of the manual adjustment to the imaging device 340.

In any or all of the processes 610, 614, and 618, the applicable correction can be determined by solving for the correction in Equation 6.

At process 622, a first virtual target position 514 of the imaging device reference point 430 is determined. In some embodiments, the first virtual target position 514 can be determined by scaling a delta of the hand-operated controller reference point 420 with respect to the hand-operated controller baseline reference point 506 by a scaling factor, according to Equation 2.

At process 624, the control system determines whether the first virtual target position 514 can be achieved. As described, in some embodiments, the first virtual follower device 520 can be virtually moved towards the first virtual target position 514. This enables determination of whether virtual ROM limits are violated. The virtual ROM limits correspond to actual ROM limits of the imaging device 340 and/or the repositionable structure on which the imaging device 340 is mounted. As used herein, "moved towards" includes motion that moves toward the target, regardless of if that motion achieves the target.

Figure 7:
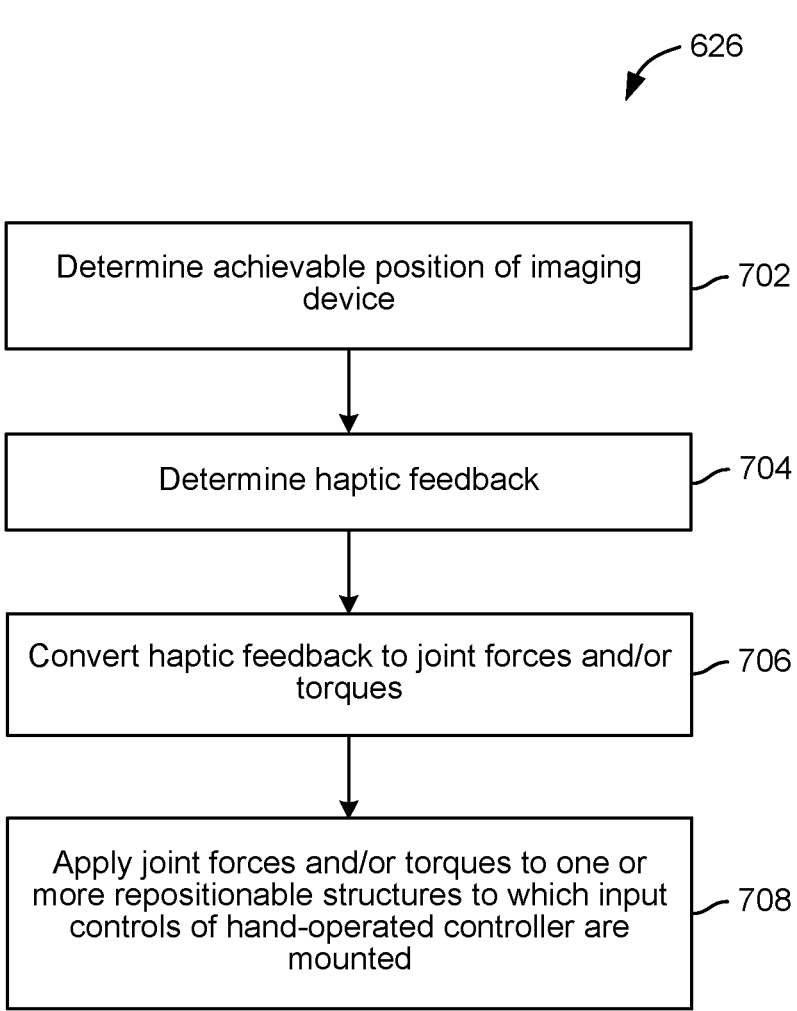
FIG. 7 illustrates in greater detail one process of the method of FIG. 6B, according to various embodiments.

If the first virtual target position 514 determined at process 622 cannot be achieved because the virtual ROM limits are violated, then an achievable position is determined at process 626. Also, haptic feedback may be provided to the hand-operated controller 320 at process 626. FIG. 7 illustrates in greater detail process 626, according to various embodiments. In some embodiments, processes 702-708 are performed separately for each of a number of axes (e.g., each of the $x_h$, $y_h$, and $z_h$ axes).

As shown, at process 702, an achievable position of the imaging device 340 is determined. Once again, the achievable position may be determined, based on the first virtual target position 514 of the imaging device reference point 430, as a position of the imaging device 340 that can be achieved while satisfying the virtual ROM limits associated with the first virtual follower device 520.

At process 704, haptic feedback is determined. In some examples, the haptic feedback can be determined as a force that is a function of a difference between a delta of the imaging device reference point 430 and a target delta of the imaging device reference point 430. The delta may be associated with the achievable position of the imaging device 340. The target delta may be determined based on the delta of the hand-operated controller reference point 420, such as in accordance with to Equation 3.

At process 706, the haptic feedback is converted to joint forces and/or torques. In some examples, the haptic feedback can be converted via inverse kinematics to joint forces and/or torques for joints of one or more repositionable structures to which the input devices 322, 324 are mounted.

At process 708, the joint forces and/or torques are applied to the repositionable structure(s) to which the input devices 322, 324 of the hand-operated controller 320 are mounted. In some examples, one or more commands may be generated and sent to the controllers for the joints in the repositionable structure(s) to which the input devices 322, 324 are mounted to provide the joint forces and/or torques.

Figure 8:
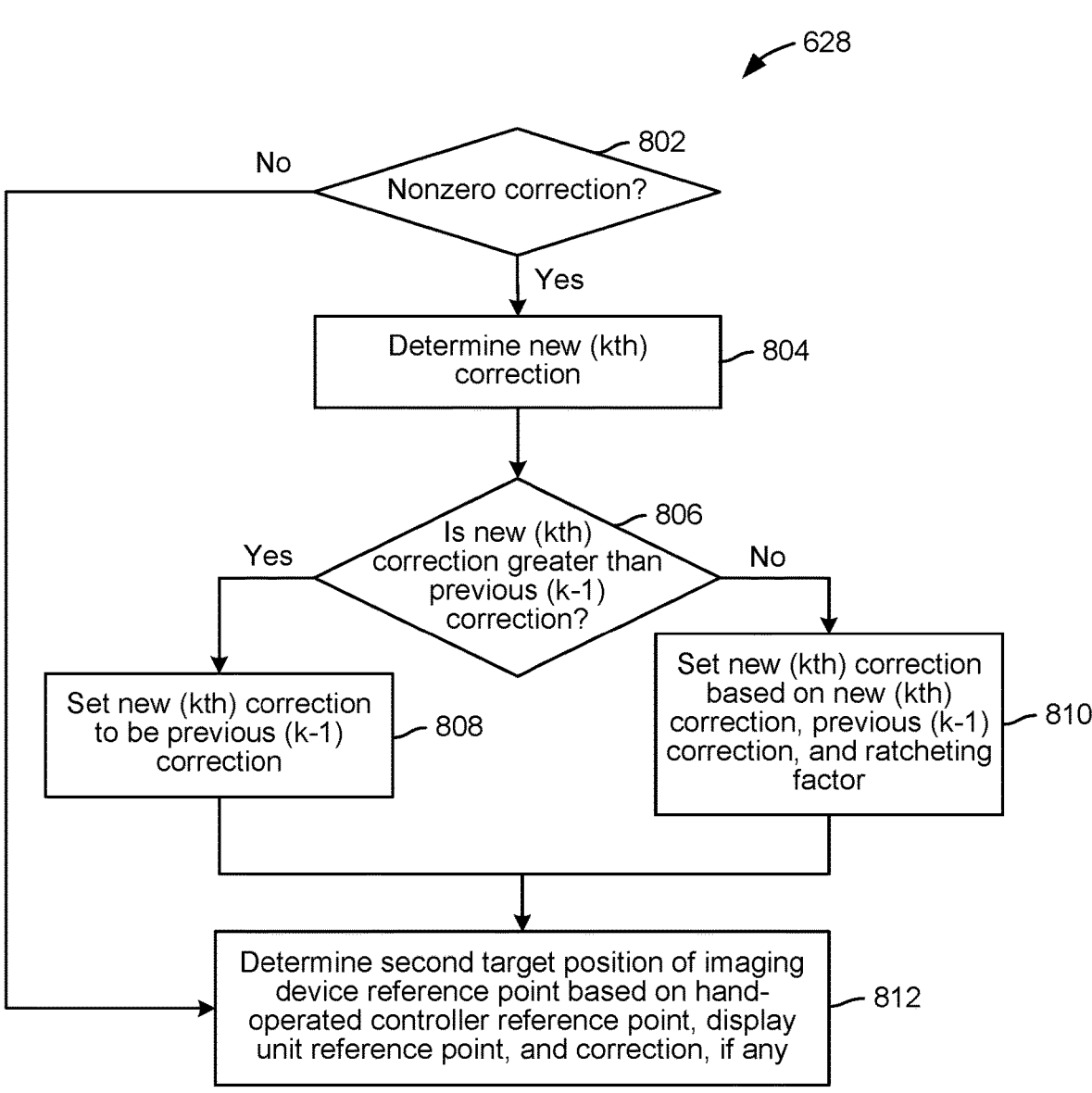
FIG. 8 illustrates in greater detail another process of the method of FIG. 6B, according to various embodiments.

Returning to FIG. 6, at process 628, a second virtual target position 518 of the imaging device reference point 430 is determined. FIG. 8 illustrates process 628 in greater detail, according to various embodiments. In some embodiments, processes 802-812 are performed separately for each of a number of axes (e.g., each of the $x_i$, $y_i$, and $z_i$ axes). As shown, at process 802, if a nonzero correction from a previous movement cycle is identified, then the method 600 continues to process 804, where a new (kth) correction is determined. As described, the new (kth) correction can be the correction in Equation 6 that is determined in response to manual repositioning of the input devices 322, 324 of the hand-operated controller 320 and/or the display unit 310 for ergonomic reasons, and/or manual repositioning of the imaging device 340.

At process 806, if a magnitude of the new (kth) correction is greater than a magnitude of the previous (k−1) correction, then at process 808, the correction is set to be the previous (k−1) correction. On the other hand, if the magnitude of the new (kth) correction is not greater than a magnitude of the previous (k−1) correction, then at process 810, the correction is set based on the new (kth) correction, the previous (k−1) correction, and a ratcheting factor. In some examples, processes 806-810 can be implemented according to Equation 7.

If $|correction_k|>|correction_{k-1}|$ Then $correction_k=correction_{k-1}$

Else $$correction_k=r\times correction_k+(1-r)\times correction_{k-1}, \quad \text{Equation 7}$$

where r is a ratcheting factor $0<r\leq1$. In some examples, r may be selected based on one or more of operator preference, a type of the display unit 310, a type of the imaging device 340, a procedure being performed, and/or the like.

Subsequent to processes 808 and 810, or if no correction is identified at process 802, the first target position of the imaging device reference point 430 is determined based on the hand-operated controller reference point and the correction, if any, at process 812. In some examples, process 812 can be implemented according to Equation 6, described above in conjunction with FIG. 5. In some examples, the ratcheting factor r may be set to 1. In such cases, the imaging device reference point 430 (and the image that the operator sees) would not move, until the correction is eliminated and the imaging device reference point 430 directly follows the display unit reference point 400 and the hand-operated controller reference point 420, according to Equation 1. In addition, by permitting the correction to only change to a smaller number, the correction converges to zero.

Returning to FIG. 6, at process 630, the control system determines whether the second virtual target position 518 can be achieved. As described, in some embodiments, the second virtual follower device 530 can be virtually moved towards the second virtual target position 518. This enables determination of whether virtual ROM limits are violated. The virtual ROM limits correspond to actual ROM limits.

If the second virtual target position 518 can be achieved, then, at process 632, the imaging device 340 is actuated based on the second virtual target position 518 of the imaging device reference point 430. In some examples, such as when the imaging device 340 is included in the endoscope described above in conjunction with FIG. 1, inverse kinematics can be used to determine joint positions of the imaging device 340 and/or the repositionable structure to which the imaging device 340 is mounted, so that the imaging device reference point 430 moves toward the target position determined according to process 628. In such cases, appropriate commands can be generated and transmitted to the controllers for the joints of the imaging device 340 and/or the repositionable structure to which the imaging device 340 is mounted. In other examples, the imaging device 340 can be repositioned in any technically feasible manner.

Figure 9:
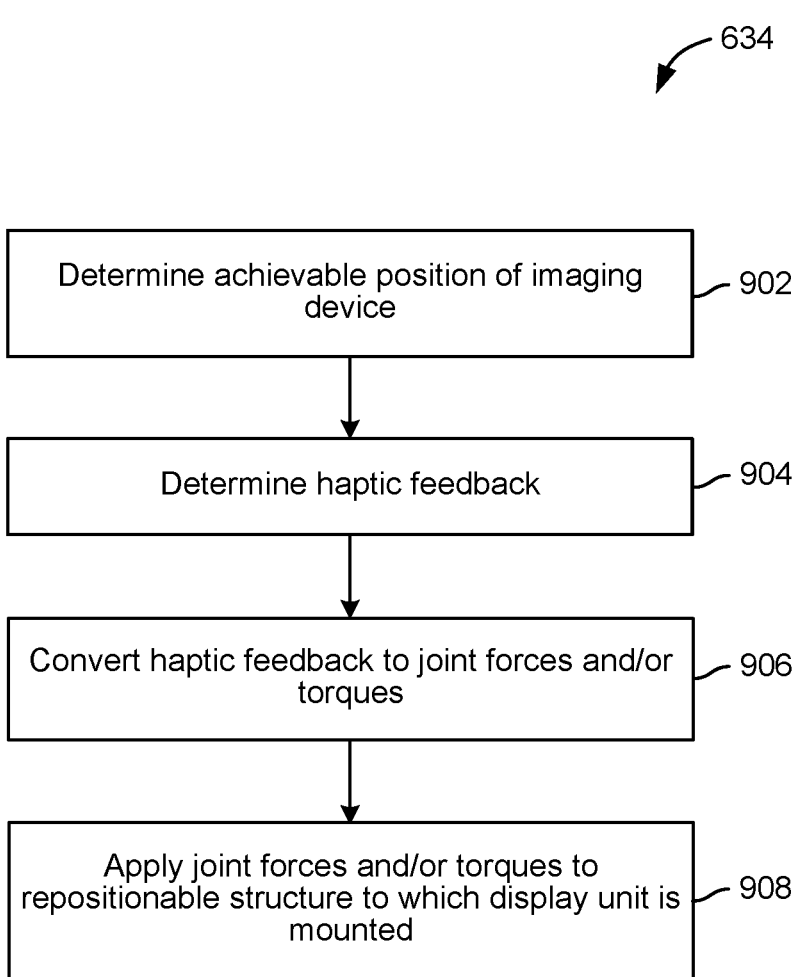
FIG. 9 illustrates in greater detail another process of the method of FIG. 6B, according to various embodiments.

On the other hand, if the second virtual target position 518 cannot be achieved, then at process 634, an achievable position is determined. Then, the imaging device 340 is actuated to or towards the achievable position. Haptic feedback may be provided to the display unit 310. FIG. 9 illustrates in greater detail process 634, according to various embodiments. In some embodiments, processes 902-908 are performed separately for each of a number of axes (e.g., each of the $x_d$, $y_d$, and $z_d$ axes).

As shown, at process 902, an achievable position of the imaging device 340 is determined. As described, in some embodiments, the achievable position may be determined, based on the second virtual target position 518 of the imaging device reference point 430, as a position of the imaging device 340 that can be achieved while satisfying virtual ROM limits associated with the second virtual follower device 530.

At process 904, haptic feedback is determined. In some examples, the haptic feedback can be determined as a force that is proportional to a difference between a delta associated with a position of the imaging device reference point 430 that can be achieved, determined using the second virtual follower device 530, and a delta associated with the position of the second virtual target position 518 by applying a scaling factor, according to Equation 4.

At process 906, the haptic feedback is converted to joint forces and/or torques. In some examples, the haptic feedback can be converted via inverse kinematics to joint forces and/or torques for joints of the repositionable structure to which the display unit 310 is mounted. In other examples, the haptic feedback may be converted to any technically feasible form(s), such as vibration of a head-mounted device.

At process 908, the joint forces and/or torques (or other form(s) of haptic feedback) are applied to the repositionable structure to which the display unit 310 is mounted (or otherwise). In some examples, one or more commands may be generated and sent to the controllers for the joints in the repositionable structure to which the display unit 310 is mounted to provide the joint forces and/or torques (or other form(s) of haptic feedback).

Returning to FIG. 6, after the imaging device 340 is actuated to or towards the new position by either process 632 or 634, a next movement cycle begins by returning to process 604.

Advantageously, the disclosed embodiments permit the motion of a repositionable imaging device to follow the motion of multiple input modalities that are being tracked as an operator controls those input modalities. The disclosed embodiments also determine which of multiple input modalities the repositionable imaging device is unable to follow so that haptic feedback can be provided to resist further attempts by the operator to move the identified input modalit(ies) in the manner that cannot be followed. In addition, the disclosed embodiments avoid discontinuities when the operator makes an ergonomic adjustment to the input modalities or a manual repositioning of the imaging device, which can be confusing to the operator.

One or more of the processes the method shown in FIGS. 6 to 9 may be partially or wholly implemented in the form of executable code stored on non-transitory, tangible, machine readable media that when run by one or more processors (e.g., the processor 150 in control system 140) may cause the one or more processors to perform one or more of the processes of method 600 and/or the processes of any of FIGS. 6, 7, and 8 In some embodiments, the processes may be performed by one or more modules, such as control module 170 in the control system 140. In some embodiments, method 600 may include additional processes, which are not shown. Some common forms of machine readable media that may include the processes of method 600 and/or the processes of FIGS. 6, 7, and/or 8 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A computer-assisted device comprising:
   a first repositionable structure configured to support an imaging device; and
   a control system coupled to the first repositionable structure;
   wherein the control system is configured to:
   determine a position of a first reference point associated with a first input modality;
   in a first mode, determine a position of a target reference point for the imaging device based on at least the first reference point;
   in a second mode:
      determine a position of a second reference point associated with a second input modality, and
      determine the position of the target reference point based on at least the position of the first reference point and the position of the second reference point;
   determine a movement of the first repositionable structure that moves the imaging device such that a third reference point associated with the imaging device moves toward the target reference point; and
   cause actuation of the first repositionable structure based on the determined movement;
   wherein:
   the first input modality comprises a hand-operated controller and the second input modality comprises one or more hand input sensors of a display unit, or
   the first input modality comprises the one or more head input sensors of the display unit and the second input modality comprises the hand-operated controller.

2. The computer-assisted device of claim 1, wherein:
   the first input modality comprises the hand-operated controller, and
   the second input modality comprises the one or more head input sensors of the display unit.

3. The computer-assisted device of claim 1, wherein:

the first input modality comprises the one or more head input sensors of the display unit, the first reference point is offset from the display unit by being in front of the display unit in a direction away from an operator, the second input modality comprises the hand-operated controller, the hand-operated controller comprises a first input control and a second input control, the second reference point is at a midpoint between the first and second input controls, and the third reference point is offset from the imaging device by being in front of the imaging device in a direction of a field of view of the imaging device.

4. The computer-assisted device of claim 1, wherein:

the imaging device and the first repositionable structure configured to support the imaging device together have a first plurality of degrees of freedom, the display unit and a second repositionable structure configured to support the display unit together have a second plurality of degrees of freedom different from the first plurality of degrees of freedom, and an input control of the hand-operated controller and a third repositionable structure configured to support the input control together have a third plurality of degrees of freedom different from the first plurality of degrees of freedom.

5. The computer-assisted device of claim 4, wherein the first plurality of degrees of freedom differ in number from the second plurality of degrees of freedom and the third plurality of degrees of freedom, or wherein the first plurality of degrees of freedom includes one or more degrees of freedom that is not matched by the second plurality of degrees of freedom or the third plurality of degrees of freedom.

6. The computer-assisted device of claim 1, further comprising:

another repositionable structure configured to support a tool, wherein the control system is further configured to, in a third mode, cause actuation of the another repositionable structure to move the tool in response to input received via the second input modality.

7. The computer-assisted device of claim 1, wherein the control system is further configured to, in a third mode:

determine the position of the second reference point associated with the second input modality, determine a position of a fourth reference point associated with a third input modality, and determine the position of the target reference point based on at least the position of the first reference point, the position of the second reference point, and the position of the fourth reference point.

8. The computer-assisted device of claim 1, wherein, to determine the position of the target reference point based on at least the position of the first reference point and the position of the second reference point, the control system is configured to:

add a first scaled difference to a second scaled difference, the first scaled difference being a difference between the position of the first reference point and a baseline reference point of the first input modality scaled by a first scaling factor, and the second scaled difference being a difference between the position of the second reference point and a baseline reference point of the second input modality scaled by a second scaling factor.

9. The computer-assisted device of claim 8, wherein the control system is further configured to:

determine the baseline reference point of the first input modality based on the position of the first reference point at an entry to the first mode;

determine the baseline reference point of the second input modality based on the position of the second reference point at an entry to a third mode; and determine the baseline reference point of the imaging device based on a configuration of the imaging device at the entry to the first mode or the entry to the third mode.

10. The computer-assisted device of claim 9, wherein the control system is further configured to:

in the third mode, determine the position of the second reference point associated with the second input modality, and determine the position of the target reference point based on at least the position of the second reference point.

11. The computer-assisted device of claim 1, wherein the control system is further configured to:

determine whether the target reference point can be achieved using a virtual follower device; and in response to determining that the target reference point cannot be achieved:

determine haptic feedback based on a difference between an achievable position of the third reference point and the target reference point, determine joint forces or torques for joints in a second repositionable structure configured to support the first input modality or a third repositionable structure configured to support the second input modality based on the haptic feedback, and cause actuation of the joints of the second repositionable structure or the third repositionable structure based on the determined joint forces or torques.

12. The computer-assisted device of claim 1, wherein the control system is further configured to, in response to determining that the first repositionable structure cannot achieve the determined movement:

determine haptic feedback based on a difference between an achievable movement of the first repositionable structure and the determined movement;

determine joint forces or torques for joints in a second repositionable structure configured to support the first input modality based on the haptic feedback; and cause actuation of the joints of the second repositionable structure based on the determined joint forces or torques.

13. The computer-assisted device of claim 1, wherein the control system is further configured to:

in response to identifying a manual adjustment to the first input modality:

set a first baseline reference point of the first input modality to the position of the first reference point at a completion of the manual adjustment to the first input modality, set a first correction distance based on a difference between the second reference point and a first baseline reference point of the second input modality, and based on a difference between the third reference point and a first baseline reference point of the imaging device, and modify the first correction distance by a ratcheting factor; or in response to identifying a manual adjustment to the second input modality:

set a second baseline reference point of the second
input modality to the position of the second reference
point at a completion of the manual adjustment to the
second input modality, set a second correction distance based on a difference
between the first reference point and a second base-
line reference point of the first input modality, and
based on a difference between the third reference
point and a second baseline reference point of the
imaging device, and modify the second correction distance by the ratcheting
factor; or in response to identifying a manual adjustment to the
imaging device:

set a third baseline reference point of the imaging
device to the position of the third reference point at
a completion of the manual adjustment to the imag-
ing device, set a third correction distance based on a difference
between the first reference point and a third baseline
reference point of the first input modality, and based
on a difference between the second reference point
and a third baseline reference point of the second
input modality, and modify the third correction distance by the ratcheting
factor.

14. A method of operating a computer-assisted device
comprising a first repositionable structure and one or more
processors, the one or more processors communicatively
coupled to the first repositionable structure, the method
comprising:

determining, by the one or more processors, a position of
a first reference point associated with a first input
modality;

in a first mode, determining, by the one or more proces-
sors, a position of a target reference point for an
imaging device supported by a first repositionable
structure of a computer-assisted device based on at
least the first reference point;

in a second mode:

determining, by the one or more processors, a position
of a second reference point associated with a second
input modality, and determining the position of the target reference point
based on at least the position of the first reference
point and the position of the second reference point;

determining, by the one or more processors, a movement
of the first repositionable structure that moves the
imaging device such that a third reference point asso-
ciated with the imaging device moves toward the target
reference point; and causing, by the one or more processors, actuation of the
first repositionable structure based on the determined
movement, wherein:

the first input modality comprises a hand-operated
controller and the second input modality comprises
one or more head input sensors of a display unit, or
the first input modality comprises the one or more head
input sensors of the display unit and the second input
modality comprises the hand-operated controller.

15. The method of claim 14, wherein:
the first input modality comprises the one or more head
input sensors of the display unit,
the first reference point is offset from the display unit by
being in front of the display unit in a direction away
from an operator, the second input modality comprises the hand-operated
controller, the hand-operated controller comprises a first input con-
trol and a second input control, the second reference point is at a midpoint between the
first and second input controls, and the third reference point is offset from the imaging device
by being in front of the imaging device in a direction of
a field of view of the imaging device.

16. The method of claim 14, further comprising:
in a third mode, causing actuation of another reposition-
able structure to move a tool in response to input
received via the second input modality,
wherein the another repositionable structure is configured
to support the tool.

17. The method of claim 14, wherein determining the
position of the target reference point based on at least the
position of the first reference point and the position of the
second reference point comprises:

adding a first scaled difference to a second scaled differ-
ence, the first scaled difference being a difference between the
position of the first reference point and a baseline
reference point of the first input modality scaled by a
first scaling factor, and the second scaled difference being a difference between
the position of the second reference point and a base-
line reference point of the second input modality scaled
by a second scaling factor.

18. The method of claim 14, further comprising,
in response to identifying a manual adjustment to the first
input modality:

setting a first baseline reference point of the first input
modality to the position of the first reference point at
a completion of the manual adjustment to the first
input modality, setting a first correction distance based on a difference
between the second reference point and a first base-
line reference point of the second input modality, and
based on a difference between the third reference
point and a first baseline reference point of the
imaging device, and modifying the first correction distance by a ratcheting
factor; or in response to identifying a manual adjustment to the
second input modality:

setting a second baseline reference point of the second
input modality to the position of the second reference
point at a completion of the manual adjustment to the
second input modality, setting a second correction distance based on a differ-
ence between the first reference point and a second
baseline reference point of the first input modality,
and based on a difference between the third reference
point and a second baseline reference point of the
imaging device, and modifying the second correction distance by the ratch-
eting factor; or in response to identifying a manual adjustment to the
imaging device:

setting a third baseline reference point of the imaging
device to the position of the third reference point at
a completion of the manual adjustment to the imag-
ing device, setting a third correction distance based on a difference
between the first reference point and a third baseline
reference point of the first input modality, and based on a difference between the second reference point and a third baseline reference point of the second input modality, and modifying the third correction distance by the ratcheting factor.

19. One or more non-transitory machine-readable media comprising a plurality of machine-readable instructions which, when executed by one or more processors of a computer-assisted device comprising a first repositionable structure, are adapted to cause the one or more processors to perform a method comprising:

determining a position of a first reference point associated with a first input modality, wherein the first input modality comprises one of a hand-operated controller or one or more head input sensors of a display unit;

in a first mode, determining a position of a target reference point for an imaging device supported by a first repositionable structure of a computer-assisted device based on at least the first reference point;

in a second mode:

determining a position of a second reference point associated with a second input modality, and determining the position of the target reference point based on at least the position of the first reference point and the position of the second reference point;

determining a movement of the first repositionable structure that moves the imaging device such that a third reference point associated with the imaging device moves toward the target reference point; and causing actuation of the first repositionable structure based on the determined movement;

wherein:

the first input modality comprises a hand-operated controller and the second input modality comprises one or more head input sensors of a display unit, or

the first input modality comprises the one or more head input sensors of the display unit and the second input modality comprises the hand-operated controller.

20. The one or more non-transitory machine-readable media of claim 19, wherein:

the first input modality comprises the one or more head input sensors of the display unit, the first reference point is offset from the display unit by being in front of the display unit in a direction away from an operator, the second input modality comprises the hand-operated controller, the hand-operated controller comprises a first input control and a second input control, the second reference point is at a midpoint between the first and second input controls, and the third reference point is offset from the imaging device by being in front of the imaging device in a direction of a field of view of the imaging device.

21. The one or more non-transitory machine-readable media of claim 19, wherein determining the position of the target reference point based on at least the position of the first reference point and the position of the second reference point comprises:

adding a first scaled difference to a second scaled difference, the first scaled difference being a difference between the position of the first reference point and a baseline reference point of the first input modality scaled by a first scaling factor, and the second scaled difference being a difference between the position of the second reference point and a baseline reference point of the second input modality scaled by a second scaling factor.

* * * * *